US012735428B2

(12) United States Patent
Riedl et al.

(10) Patent No.: US 12,735,428 B2
(45) Date of Patent: Sep. 15, 2026

(54) 12-EPI-MUTILIN COMPOUNDS AND USES THEREOF

(71) Applicant: ARIVA MED GMBH, Vienna (AT)

(72) Inventors: Rosemarie Riedl, Vienna (AT); Susanne Paukner, Vienna (AT); Wolfgang Wicha, Bruck an der Leitha (AT); Klaus Thirring, Vienna (AT); Dirk Strickmann, Purkersdorf (AT); Michael Hafner, Vienna (AT)

(73) Assignee: ARIVA MED GMBH, Vienna (AT)

( * ) Notice: Subject to any disclaimer, the term of this patent is extended or adjusted under 35 U.S.C. 154(b) by 511 days.

(21) Appl. No.: 18/286,958

(22) PCT Filed: Apr. 15, 2022

(86) PCT No.: PCT/EP2022/060174

§ 371 (c)(1),
(2) Date: Oct. 13, 2023

(87) PCT Pub. No.: WO2022/219182

PCT Pub. Date: Oct. 20, 2022

(65) Prior Publication Data

US 2024/0208989 A1 Jun. 27, 2024

(30) Foreign Application Priority Data

Apr. 16, 2021 (EP) .................................... 21168830

(51) Int. Cl.

| | |
|---|---|
| ***C07D 493/04*** | (2006.01) |
| ***A61K 31/443*** | (2006.01) |
| ***A61K 31/497*** | (2006.01) |
| ***A61K 31/506*** | (2006.01) |
| ***A61P 31/04*** | (2006.01) |

(52) U.S. Cl.
CPC .......... *C07D 493/04* (2013.01); *A61K 31/443* (2013.01); *A61K 31/497* (2013.01); *A61K 31/506* (2013.01); *A61P 31/04* (2018.01)

(58) Field of Classification Search
CPC ..... A61P 31/04; C07D 493/04; A61K 31/443; A61K 31/497; A61K 31/506
See application file for complete search history.

(56) References Cited

U.S. PATENT DOCUMENTS 9,701,628 B2 * 7/2017 Thirring ............... A61K 31/495

FOREIGN PATENT DOCUMENTS

| | | | |
|---|---|---|---|
| WO | 03/082260 | A2 | 10/2003 |
| WO | 2015/110481 | A1 | 7/2015 |
| WO | 2021/209596 | A1 | 10/2021 |
| WO | 2021/219399 | A1 | 11/2021 |

OTHER PUBLICATIONS

Fazakerley, N.J. and Procter, D.J., 2014. Synthesis and synthetic chemistry of pleuromutilin. Tetrahedron, 70(39), pp. 6911-6930. (Year: 2014).*

(Continued)

*Primary Examiner* — James H Alstrum-Acevedo
*Assistant Examiner* — Carolyn L. Ladd
(74) *Attorney, Agent, or Firm* — Venable LLP

(57) ABSTRACT

A compound of formula (I)

(I)

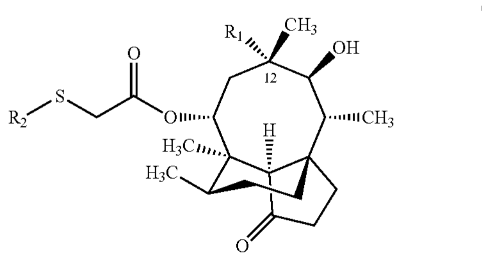

wherein $R_1$ is wherein A is hydrogen atom or a $(C_{1-6})$alkyl, and
wherein any Q is independently from each other a nitrogen atom or CH,
wherein $R_2$ is the compound for use as a medicament and a pharmaceutical composition comprising the compound as well as a method of treatment or prevention a disease mediated by microbes making use thereof.

13 Claims, No Drawings

(56) References Cited

OTHER PUBLICATIONS

Goethe, O., Heuer, A., Ma, X., Wang, Z. and Herzon, S.B., 2019. Antibacterial properties and clinical potential of pleuromutilins. Natural product reports, 36(1), pp. 220-247 (Year: 2019).*
Berner et al., "Synthese ab-trans-anellierter derivate des tricyclischen diterpens pleuromutilin durch intramolekulare 1,5-hydrid-verschiebung," Tetrahedron, vol. 36, No. 12, pp. 1807-1811 (1980).
O'Brien, "Development of treatments for gonorrhoea: Addressing the global public health need," US FDA Workshop, "Development Considerations of Antimicrobial Drugs for the Treatment of Gonorrhea," Apr. 23, 2021.
Long et al., "The Cfr rRNA Methyltransferase Confers Resistance to Phenicols, Lincosamides, Oxazolidinones, Pleuromutilins, and Streptogramin A Antibiotics," Antimicrobial Agents and Chemotherapy, vol. 50, No. 7, pp. 2500-2505 (2006).
Mendes et al., "Low Prevalence of Gram-Positive Isolates Showing Elevated Lefamulin MIC Results during the SENTRY Surveillance Program for 2015-2016 and Characterization of Resistance Mechanisms," Antimicrobial Agents and Chemotherapy, vol. 63, No. 4, e02158-18, pp. 1-9 (2019).
Wu et al., "In vitro Activity of Lefamulin Against the Common Respiratory Pathogens Isolated From Mainland China During 2017-2019," Frontiers in Microbiology, vol. 11, Article 578824, pp. 1-8 (2020).
Transcript, US FDA Workshop, "Development Considerations of Antimicrobial Drugs for the Treatment of Gonorrhea," Apr. 23, 2021.
The Merck Index, 12th edition, item 7694 (1996).
Paukner et al., "Pleuromutilins: Potent Drugs for Resistant Bugs-Mode of Action and Resistance," Cold Spring Harbor Prespectives in Medicine, vol. 7, a027110, pp. 1-15 (2017).
Dever at al., "In vitro antimicrobial susceptibility testing of Borrelia burgdorferi: a microdilution MIC method and time-kill studies," J. Clinical Microbiology, vol. 30, No. 10, pp. 2692-2697 (1992).
Feng et al., "Identification of novel activity against Borrelia burgdorferi persisters using an FDA approved drug library," Emerging Microbes and Infections, vol. 3, e49, pp. 1-8 (2014).

* cited by examiner

12-EPI-MUTILIN COMPOUNDS AND USES THEREOF

CROSS REFERENCE TO RELATED APPLICATIONS

The present application is a national-stage entry under 35 U.S.C. § 371 of International Patent Application No. PCT/EP2022/060174, published as WO 2022/219182 A1, filed Apr. 15, 2022, which claims priority to EP 21168830.4, filed Apr. 16, 2021, the entire disclosure of each of which is hereby incorporated by reference.

BACKGROUND OF THE INVENTION

Field of the Invention

The invention relates to specific 12-epi-mutilin compounds and their use as medicament.

DESCRIPTION OF RELATED ART (Pleuro)mutilins are compounds of e.g. formulae:

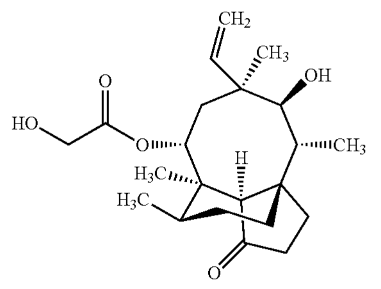

Pleuromutilin

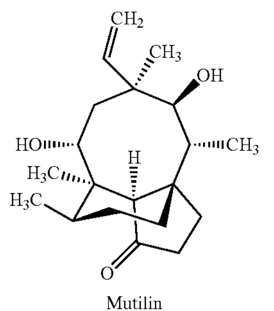

Mutilin

Pleuromutilin is a naturally occurring antibiotic, produced e.g. by the basidiomycetes *Pleurotus mutilus* and *P. passeckerianus*, see e.g. The Merck Index, 12th edition, item 7694.

Pharmaceutical active compounds derived from pleuromutilin (semi synthetic compounds) are inhibitors of ribosomal protein synthesis in bacteria. Representatives of semi-synthetic pleuromutilins for human use are Retapamulin (approved as AltargoP®, AltabaxP®), a topical agent approved for short term treatment of impetigo and infected small lacerations, abrasions or sutured wounds, and Lefamulin (approved as Xenleta®) for the treatment of adults with community-acquired bacterial pneumonia (CABP). Tiamulin (Denagard®) and Valnemulin (Econor®) are two other semi-synthetic pleuromutilin derivatives which have been used systemically as antibiotics in veterinary medicine for many years.

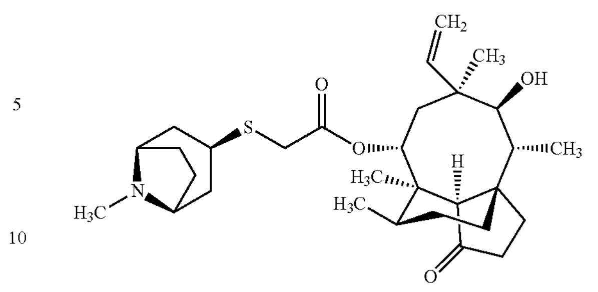

Retapamulin

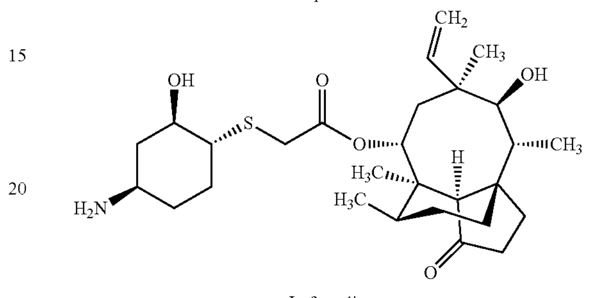

Lefamulin

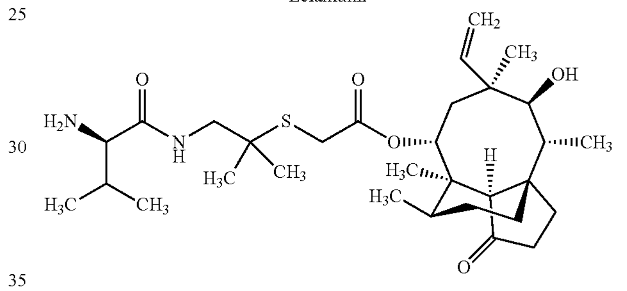

Valnemulin

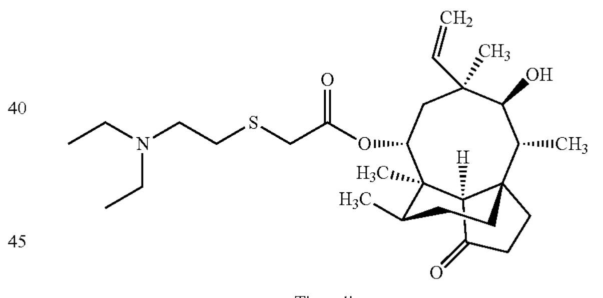

Tiamulin

Approved semisynthetic compounds derived from pleuromutilin have shown excellent activity against bacterial organisms which include inter alia *Streptococcus pneumoniae, Haemophilus influenzae, Staphylococcus aureus* (including MRSA), *Moraxella catarrhalis, Legionella pneumophila, Chlamydophila pneumoniae* and *Mycoplasma pneumoniae.*

Lefamulin's activity covers common respiratory microbes and occurrence of isolates exhibiting resistances is low (Mendes R E, Paukner S, Doyle T B, Gelone S P, Flamm R K, Sader H S. *Antimicrob Agents Chemother.* 2019 63(4), e02158-18; Wu, S.; Zheng, Y.; Guo Y.; Yin, D.; Zhu, D.; Hu, F. Frontiers in Microbiology, 2020, 11, 2314). However, individual bacterial phenotypes with resistance against pleuromutilin antibiotics (Long, K. S.; Poehlsgaard, J.; Kehrenberg, C.; Schwarz, S.; Vester, B. *Antimicrob Agents Chemother.* 2006, 50(7), 2500-2505) and Lefamulin (Mendes R E, Paukner S, Doyle T B, Gelone S P, Flamm R K, Sader H S. *Antimicrob Agents Chemother.* 2019 63(4), e02158-18) have been described. Potential acquired Lefamulin resistance mechanisms identified to date include the following (sorted by epidemiological relevance): i) target protection by ABC-F proteins e.g. vga(A-E) of *Staphylococcus* spp., lsa(E) of *S. agalactiae, Enterococcus* spp., and *S. aureus*, sal(A) of coagulase-negative *Staphylococcus* spp., ii) Modification of the target e.g. Mutations in rplC and rplD genes encoding ribosomal proteins located outside of PTC, mutations in domain V of the 23S rRNA, or methylation of position A2503 of the 23S rRNA in the PTC mediated by the Cfr methyl transferase (encoded by cfr) (Paukner S, Riedl R. Pleuromutilins: Potent Drugs for Resistant Bugs-Mode of Action and Resistance. Cold Spring Harb Perspect Med. 2017 Jan. 3; 7(1):a027110. doi: 10.1101/cshperspect.a027110. PMID: 27742734; PMCID: PMC5204327). Lefamulin was also subject of a workshop by US FDA on "Development Considerations of Antimicrobial Drugs for the Treatment of Gonorrhea" held on Apr. 23, 2021. The slides of a talk entitled "*Development Considerations for a Syndromic Approach to Uncomplicated Urethritis/Cervicitis*" as well as a transcript of the workshop were thereafter made available for downloaded from the FDA webpage (https://www.fda.gov/drugs/news-events-human-drugs/development-considerations-antimicrobial-drugs-treatment-gonorrhea-04232021-04232021, with content of May 26, 2021), in particular from https://www.fda.gov/media/149520/ download and https://www.fda.gov/media/148225/ download (both links accessed on Feb. 1, 2022).

In WO 2015/110481 A1 pleuromutilin derivatives are disclosed which are called "12-epi-mutilins". The term "12-epi-mutilin" means that the mutilin ring at position 12 is substituted by two substituents, the first substituent at position 12 of the mutilin ring is a methyl group which methyl group has the inverse stereochemistry compared with the stereochemistry of the methyl group at position 12 of the naturally occurring pleuromutilin ring, the second substituent at position 12 of the mutilin ring is a hydrocarbon group comprising at least one nitrogen atom, and all other substituents of the mutilin ring having the same stereochemistry compared with the stereochemistry of the substituents at the corresponding positions in the naturally occurring pleuromutilin ring; optionally in the form of a salt and/or solvate, in particular in the form of a salt.

These compounds have been found to show interesting activity against Gram-positive and Gram-negative bacteria.

A first synthetic approach towards the inverted stereochemistry was described by Berner, H. et al (Berner, H.; Schulz, G.; Schneider H. *Tetrahedron* 1980, 36, 1807-1811).

SUMMARY OF THE INVENTION

Surprisingly, new 12-epi-mutilins (examples 1-3) were found that combine interesting antibacterial activity (example 4) with remarkable metabolic stability and low cytotoxicity (examples 5 and 6).

Therefore, in one aspect the present invention relates to a compound of formula (I)

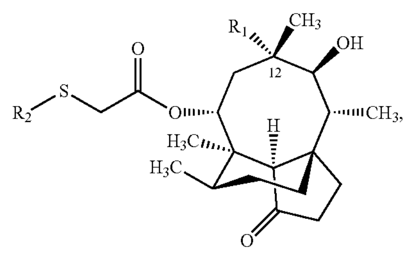

(I)

wherein $R_1$ is

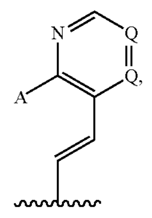

wherein A is hydrogen atom or a $(C_{1-6})$alkyl, and wherein any Q is independently from each other a nitrogen atom or CH, wherein $R_2$ is

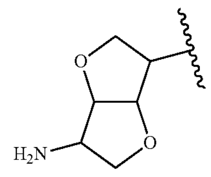 [SMILES: *C1COC2C(N)COC12]

as well as their use as medicament, in particular in the treatment and prevention of a disease mediated by bacteria.

The present invention also relates to a pharmaceutical composition comprising a compound of formula (I) as defined above.

In a further aspect, the present invention relates to a method of treatment or prevention of a disease mediated by bacteria, comprising administering a compound of formula (I) to a subject in need thereof.

DETAILED DESCRIPTION OF THE INVENTION

In a compound of formula (I), the methyl group at position 12 of the mutilin ring has the inverse stereochemistry compared with the stereochemistry of the methyl group at position 12 of the naturally occurring pleuromutilin ring, all other substituents of the mutilin ring having the same stereochemistry compared with the stereochemistry of the substituents at the corresponding positions in the naturally occurring pleuromutilin ring. The naturally occurring pleuromutilin ring is shown for example in the structure of Pleuromutilin above. Accordingly, the compounds of the present invention are so-called 12-epi-mutilins.

In a compound of formula (I) $R_1$ is

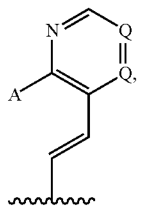

wherein A is hydrogen atom or a $(C_{1-6})$alkyl, and wherein any Q is independently from each other a nitrogen atom or CH, i.e., a heterocyclyl-ethenyl, wherein the heterocyclyl is an alkyl-substituted or unsubstituted pyridyl, pyrimidinyl, or pyrazinyl.

In a preferred embodiment, A is a $(C_{1-3})$alkyl, i.e. a $(C_{1-3})$alkyl selected from the group consisting of methyl, ethyl, 1-propyl, 2-propyl, and cyclopropyl, preferably methyl.

Even more preferably, $R_1$ is selected from the group consisting of (E)-2-(pyrimidin-5-yl)-ethenyl, (E)-2-(pyrimidin-5-yl)-ethenyl, and (E)-2-(3-methyl-pyrazin-2-yl.

In a compound of formula (I) $R_2$ is

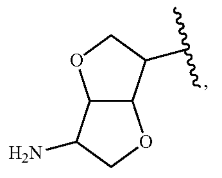 [SMILES: *C1COC2C(N)COC12]

Accordingly, the $R_2$ is an amino substituted bicyclic oxygen-containing heterocycle or systematically, $R_2$ is a 3-amino-hexahydrofuro[3,2-b]furan-6-yl.

A compound of the present invention may exist in the form of isomers and mixtures thereof, e.g. diastereoisomers and cis/trans conformers. A compound of the present invention may e.g. contain asymmetric carbon atoms and may thus exist in the form of diastereoisomers and mixtures thereof. If not indicated otherwise, any asymmetric carbon atom may be present in the (R)-, (S)- or (R,S)-configuration, preferably in the (R)- or (S)-configuration.

In a preferred embodiment, $R_2$ is derived from D-isomannide. Accordingly, $R_2$ preferably is (3S,3aR,6S,6aS)-3-amino-2,3,3a,5,6,6a-hexahydrofuro[3,2-b]furan-6-yl.

Thus, preferred compounds of the present invention are compounds of formula (II), (II)

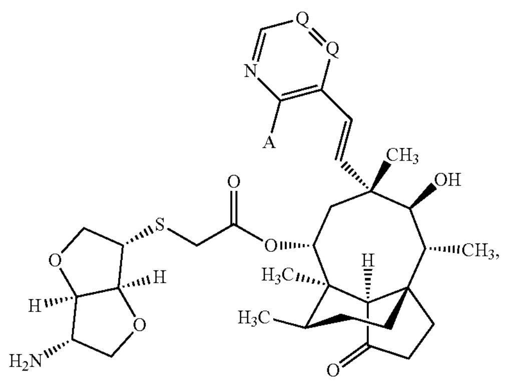

wherein A and Q are as defined above.

Particularly preferred compounds of the present invention are selected from the group consisting of compounds of formula (III) to (V)

(III)

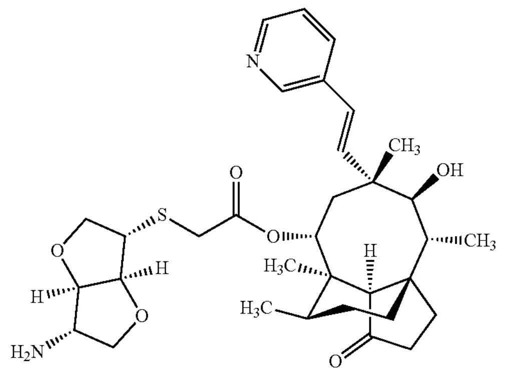

(IV)

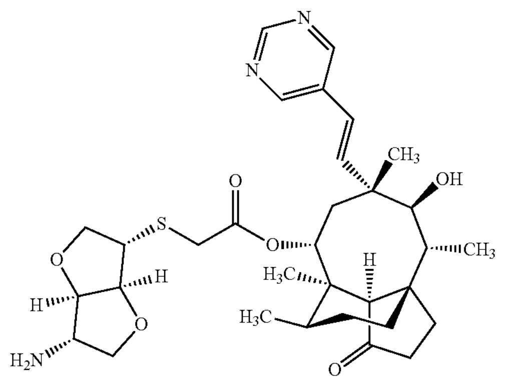

(V)

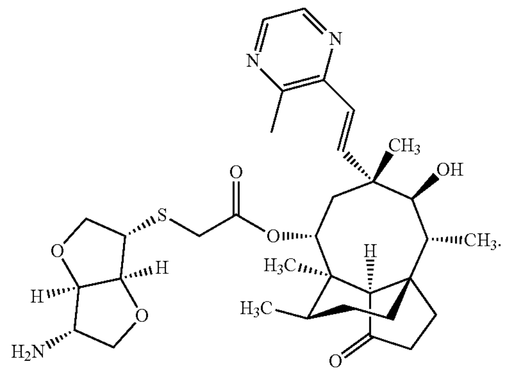

The systematic name of a compound of formula (III) is 12-epi-12-Desvinyl-14-O-{[(3S,3aR,6S,6aS)-3-amino-2,3,3a,5,6,6a-hexahydrofuro[3,2-b]furan-6-yl]sulfanylacetyl}-12-[(E)-2-(3-pyridyl)-ethenyl]-mutilin, a compound of formula (IV) is 12-epi-12-Desvinyl-14-O-{[(3S,3aR,6S,6aS)-3-amino-2,3,3a,5,6,6a-hexahydrofuro[3,2-b]furan-6-yl]sulfanylacetyl}-12-[(E)-2-(pyrimidin-5-yl)-ethenyl]-mutilin, a compound of formula (V) is 12-epi-12-Desvinyl-14-O-{[(3S,3aR,6S,6aS)-3-amino-2,3,3a,5,6,6a-hexahydrofuro[3,2-b]furan-6-yl]sulfanylacetyl}-12-[(E)-2-(3-methyl-pyrazin-2-yl)-ethenyl]-mutilin.

In one embodiment, the compound according to the invention is provided in the form of a salt and/or solvate.

The compounds of the present invention can be protonated and form a cation in an acid addition salt, such as for example a bivalent cation, such as in a dihydrochloride salt.

A salt of a compound of the present invention includes an acid addition salt. Pharmaceutically acceptable acid addition salts include salts of a compound of the present invention with an acid, e.g. fumaric acid, tartaric acid, sulphuric acid, p-toluene sulphonic acid, methane sulphonic acid, phosphoric acid, citric acid, L-malic acid, hippuric acid, D-gluconic acid, L-lactic acid, benzoic acid, hydrogenmaleic acid, hydrogen sulphuric acid, hydrogenphosphoric acid, hydrogen tartaric acid, hydrogen fumaric acid, hydrogen malic acid, hydrogen succinic acid, ethane-1,2-disulphonic acid, maleic acid, naphthalin-1,5-sulphonic acid, acetic acid, succinic acid, salicylic acid, azelaic acid, 2-[(2,6-dichlorophenyl)amino]benzene acetic acid, trifluoro acetic acid, hydrochloric acid, deuterochloric acid, preferably hydrochloric acid, acetic acid, L-lactic acid and maleic acid, more preferably hydrochloric acid.

Pharmaceutically acceptable salts are described in e.g. Stahl, P. H., Wermuth, C. G, *Handbook of Pharmaceutical Salts: Properties. Selection, and Use*, Helvetica Chimica Acta/Wiley-VCH, 2001.

A compound of the present invention in free form may be converted into a corresponding compound in the form of a salt, and vice versa. A compound of the present invention in free form or in the form of a salt and/or in the form of a solvate may be converted into a corresponding compound in free form or in the form of a salt in non-solvated form, and vice versa.

The invention also relates to a compound of the present invention, optionally in the form of a pharmaceutically acceptable salt and/or solvate, for use as a medicament.

The compounds of the present invention exhibit pharmacological activity and are therefore useful as medicament.

For example, the compounds of the present invention show antimicrobial, e.g. antibacterial activity against

- Gram-positive bacteria, such as coagulase positive staphylococci, e.g. *Staphylococcus aureus*, including coagulase negative staphylococci, e.g. *Staphylococcus epidermidis, Staphylococcus haemolyticus*, and streptococci, e.g. *Streptococcus pyogenes, Streptococcus pneumoniae*, and
- against Gram-negative bacteria such as *Moraxella*, e.g. *Moraxella catarrhalis*, and *Haemophilus*, e.g. *Haemophilus influenzae* as well as against spirochetes, i.e. bacteria from the phylum of spirochaetes such as e.g. *Borreliella* spp.

Accordingly, in a further aspect the present invention provides a compound of the present invention for use in the treatment and prevention of a disease mediated by bacteria.

In one embodiment, the disease is mediated by bacteria selected from the group consisting of

- Gram-positive bacteria including
  - staphylococci, e.g. *Staphylococcus aureus,*
  - streptococci, e.g. *Streptococcus pneumoniae*, ß-hemolytic or viridans group *Streptococcus* spp.
  - enterococci, e.g. *Enterococcus faecium.*
  - Peptostreptococci, e.g. *Peptostreptococcus anaerobius,*
  - Clostridia, e.g. *Clostridium difficile* and *Clostridium perfringens,*
  - Cutibacteria (*Cutibacterium* spp. formerly known as *Propionibacterium* spp.), e.g. *Cutibacterium acnes, Cutibacterium avidum*, and *Cutibacterium granulosum*
  - as well as *Listeria monocytogenes, Eubacterium lentum, Finegoldia magna, Anaerococcus prevotii*, and *Peptoniphilus assaccharolyticus,* and

- Gram-negative bacteria including
  - Moraxella, e.g. *Moraxella catarrhalis,*
  - Haemophilus, e.g. *Haemophilus influenzae* and *Haemophilus parainfluenzeae,*
  - Chlamydiae, e.g. *Chlamydophila pneumoniae* and *Chlamydia trachomatis*
  - Neisseriaceae, e.g. *Neisseria gonorrhoeae,*
  - *Mycoplasma* spp., e.g. *Mycoplasma pneumoniae* and *Mycoplasma genitalium,*
  - Fusobacteria, e.g. *Fusobacterium fusiforme, Fusobacterium necrophorum, Fusobacterium mortiferum*, and *Fusobacterium varium,*
  - *Prevotella* spp., e.g. *Prevotella buccae* and *Prevotella oris*
  - *Porphyromonas* spp., e.g. *Porphyromonas gingivalis* and *Porphyromonas asaccharolytica,*
  - Legionella, e.g. *Legionella pneumophila*
  - spirochetes, more precisely bacteria selected from the phylum of Spirochaetes, e.g. *Borrelia* spp., *Borreliella* spp., *Leptospira* spp., and *Treponema* spp.
  - as well as *Bacteroides fragilis*, and *Acinetobacter lwoffii.*

The disease may be mediated by Gram-negative or Gram-positive bacteria including aerobes, facultative anaerobes or obligatory anaerobes. In one embodiment, the disease is mediated by aerobic or facultative anaerobic bacteria, in particular aerobic or facultative anaerobic Gram-positive bacteria.

Preferably, the disease is mediated by bacteria selected from the group consisting of staphylococci and streptococci.

In particular, the disease is mediated by bacteria resistant to Lefamulin. For example, bacteria having a resistance mechanism, e.g. mediated by vga(A), lsa(E) or cfr.

In a preferred embodiment, the disease is selected from the group consisting of

- a respiratory tract infection including pneumonia, e.g. a community-acquired bacterial pneumonia (CABP) and nosocomial pneumonia,
- an infection of skin and/or soft tissue, including acute bacterial skin and skin structure infection (ABSSI),
- a systemic infection including sepsis,
- a prosthetic joint infection,
- sexually transmitted infections (STI), including syphilis,
- acne,
- Lyme Disease and relapsing fever.

More preferably, the disease is a respiratory tract infection including community-acquired pneumonia and nosocomial pneumonia, a skin and/or soft tissue infection including acute bacterial skin and skin structure infection, a sexually transmitted infection, or sepsis.

In one embodiment, the disease is mediated by spirochetes, more precisely bacteria selected from the phylum of Spirochaetes.

The phylum of Spirochaetes includes different taxonomic classes and orders. At the level of orders it includes i.a. Brachyspirales, Spirochaetales or Leptospirales. Brachyspirales include spirochetes known to cause veterinary disease including for example *Brachyspira hyodysenteriae*. Spirochaetales or Leptospirales also include bacteria mediating bacterial infections in humans. Within the order of Spirochaetales, there are the taxonomic families of Borreliaceae and Treponemataceae (among other families).

In a preferred embodiment of the present invention, the present invention concerns the use of the compounds according to the invention, in the treatment or prevention of a bacterial infection mediated by bacteria selected from the orders of Spirochaetales or Leptospirales, more preferably Spirochaetales. In a particular embodiment, the bacteria are selected from the families of Borreliaceae and Treponemataceae (both within the order of Spirochaetales).

More preferably, the bacteria are selected from the group consisting of the genera *Borrelia, Borreliella, Leptospira*, and *Treponema* preferably from the group consisting of the genera *Borreliella* and *Treponema.*

If referred to a specific genus, it is to be understood that the term includes all species and subspecies of the genus. For example, the genus *Borrelia* covers *Borrelia* spp.

Bacteria of the genus *Borrelia* within the order of Spirochaetales and the family of Borreliaceae cause Relapsing fever. The disease is characterized by relapsing fevers with spirochetes evident on blood smear and transmitted e.g. by bites of lice or soft-bodied ticks (genus *Ornithodoros*). Particular bacteria of interest include: *Borrelia crocidurae, Borrelia duttoni, Borrelia hermsii, Borrelia ispanica, Borrelia miyamotoi, Borrelia parkeri, Borrelia turicatae, Borrelia persica*, and *Borrelia recurrentis.*

Bacteria of the genus *Borreliella* were formerly referred to as *Borrelia*, however, represent an individual genus within the order of Spirochaetales and the family of Borreliaceae. Bacteria of the genus *Borreliella* cause Lyme Disease/Lyme Borreliosis. Lyme borreliosis (LB) is a tick-transmitted bacterial infection caused by some members of the spirochete group *Borreliella burgdorferi*. It is the most prevalent tick-transmitted infection in temperate areas of Europe, North America and Asia, and its geographic distribution is ever-increasing. The *B. burgdorferi* complex comprises at least 15 genospecies worldwide: still, only six are significantly pathogenic to humans. All pathogenic genospecies can cause erythema migrans, the early skin rash of LB. *B. afzelii* and *B. garinii* are the major pathogenic genospecies found in Europe and are associated with skin and neurological complications, respectively. *B. burgdorferi* sensu stricto (the major pathogenic genospecies found in North America) is present in some parts of Europe and can cause neurological and arthritic complications. In North America, *Borreliella mayonii* (also referred to as *Borrelia mayonii*) are a type of bacteria recently (2013) found that can cause Lyme disease. Based on limited information, illness caused by *B. mayonii* appears similar to that caused by *B. burgdorferi*, but with a few differences. Like *B. burgdorferi, B. mayonii* causes fever, headache, rash, and neck pain in the days after infection and can cause arthritis after a few weeks of illness. Unlike *B. burgdorferi, B. mayonii* can also cause nausea and vomiting: large, widespread rashes; and a higher concentration of bacteria in the blood. Other pathogenic genospecies have been identified in Europe: *B. bavariensis*, associated with neurological complications, and *B. spielmanii*. In a preferred embodiment, the bacteria are *Borreliella* selected from the group of the species mentioned in this paragraph, and more preferably *Borreliella burgdorferi* and *Borreliella garinii.*

In a preferred embodiment, the bacterial infection is mediated by bacteria of the family of Borreliaceae, preferably by *Borreliella* or *Borrelia*, more preferably *Borreliella*. In particular, the bacterial infection is selected from the group of Lyme Disease and Relapsing fever, preferably Lyme Disease (including Lyme Borreliosis).

Bacteria of the genus *Leptospira* within the order of Leptospirales and the family of Leptospiraceae cause Leptospirosis. Leptospirosis is a bacterial disease/infection that affects humans and animals. A rare and severe form of human Leptospirosis includes Weil's disease with symptoms like chest pain and swollen arms and legs. It often requires hospitalization. Currently, the genus *Leptospira* includes 21 named species of e.g. *Leptospira interrogans, Leptospira inadai.*

Bacteria of the genus *Treponema* within the order of Spirochaetales and the family of Treponemataceae cause various diseases in humans also referred to as treponematoses.

Syphilis is a complex systemic illness caused by the highly invasive *Treponema pallidum. Treponema pallidum* subsp *pallidum* mediates venereal syphilis (the classical form of sexually transmitted syphilis): *T. pallidum* subsp *endemicum* mediates endemic syphilis. *T. pallidum* subsp *pertenue* mediates yaws. Yaws is a common chronic infectious disease that occurs mainly in warm humid regions. The disease has many names (for example, pian, parangi, paru, frambesia tropica). Yaws usually features lesions that appear as bumps on the skin of the face, hands, feet, and genital area.

*Treponema carateum* mediates the infectious disease Pinta, a skin infection, which occurs only in the Western hemisphere, has been described in Central and South America, Cuba, and the Caribbean islands. Pinta is the most benign of the nonvenereal treponematoses, because it involves only the skin.

*Treponema denticola* is associated with the incidence and severity of human periodontal disease (treponemal peridontitis). Having elevated *T. denticola* levels in the mouth is considered one of the main etiological agents of periodontitis.

In a preferred embodiment, the bacteria are *Treponema* selected from the group of the species mentioned in the preceding paragraphs, and more preferably *Treponema pallidum.*

In a preferred embodiment, the bacterial infection is mediated by *Treponema*. In particular, the bacterial infection is selected from the group of syphilis including venereal and endemic syphilis, pinta, (treponemal) periodontitis and yaws, preferably syphilis.

A subject in need of a treatment of a disease mediated by spirochetes may be any living subject suffering from a bacterial infection mediated by spirochetes or by bacteria selected from the phylum of Spirochaetes. Especially, the subject may be a human or an animal, in particular a human. Accordingly, in one embodiment, the compound is administered (or configured for being administered) to a human.

In another aspect, the present invention provides a use of the compound for the manufacture of a medicament, in particular a medicament for treatment and prevention of the above-mentioned diseases.

In a further aspect the present invention provides a method of treatment of a disease mediated by bacteria which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.5 mg to 3 g of a compound of the present invention conveniently administered, for example, in divided doses up to four times a day. Administration may also include continuous infusion if the compound is given intravenously.

Preferably, the compound used according to the present invention is administered via inhalation, via intravenous or subcutaneous injection, or orally.

A compound of the present invention may be administered by any conventional route, for example enterally, e.g. including nasal, buccal, rectal, oral administration: parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or in free form, optionally in the form of a solvate. A compound of the present invention in the form of a salt exhibits the same order of activity as the compound in free form, optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect, the present invention provides a pharmaceutical composition comprising a compound of the present invention in free form or in the form of a pharmaceutically acceptable salt and/or in the form of a solvate in association with at least one pharmaceutical, excipient, e.g. carrier or diluent, e.g. including fillers, binders, disintegrators, flow conditioners, flow enhancers, glidants, lubricants, sugars and sweeteners, fragrances, taste maskers, preservatives, stabilizers, wetting agents and/or emulsifiers, solubilizers, salts for regulating osmotic pressure and/or buffers.

In one embodiment, the present invention provides a pharmaceutical composition comprising a compound according to the present invention, and further comprising another pharmaceutically active agent.

Such pharmaceutical compositions may be manufactured according, e.g. analogously, to a method as conventional, e.g. by mixing, spray drying, granulating, coating, dissolving or lyophilizing processes. Unit dosage form may contain, for example, from about 0.5 mg to about 2000 mg, such as 10 mg to about 1500 mg.

A subject in need of a treatment as contemplated by the present invention may be any living subject suffering from a disease mediated by bacteria. Especially, the subject may be a human or an animal.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect, the present invention provides a compound of the present invention for use as a veterinary agent.

In a further aspect, the present invention provides a compound of the present invention for the preparation of a veterinary composition which is useful as a veterinary agent.

In another aspect, the present invention provides a veterinary method for the prophylaxis and the treatment of microbial, e.g. bacterial diseases which comprises administering to a subject in need of such treatment an effective amount of a compound of the present invention, e.g. in the form of a veterinary composition.

In a further aspect, the present invention provides a compound according to the generic formula (VI)

(VI)

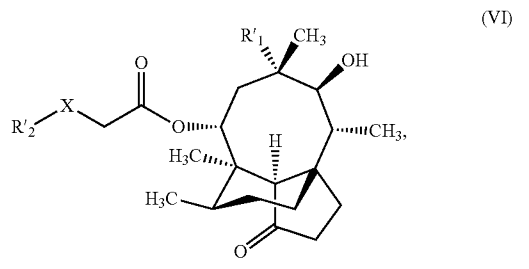

wherein the methyl group at position 12 of the mutilin ring has the inverse stereochemistry compared with the stereochemistry of the methyl group at position 12 of the naturally occurring pleuromutilin ring, all other substituents of the mutilin ring having the same stereochemistry compared with the stereochemistry of the substituents at the corresponding positions in the naturally occurring pleuromutilin ring, $R'_1$ is either $(C_{1-16})$alkyl or $(C_{2-16})$alkenyl, substituted by heterocyclyl, including aliphatic heterocyclyl and aromatic heterocyclyl comprising 1 to 4 heteroatoms selected from N, O, S, with the proviso that at least one heteroatom is a nitrogen atom, or $R'_1$ is a group of formula

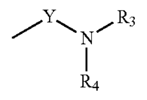

wherein Y—$N(R_3R_4)$ is $(C_{1-16})$alkyl-$N(R_3R_4)$, $(C_{1-16})$alkyl-$(C_{6-14})$aryl-$N(R_3R_4)$, $(C_{1-16})$alkyl-$(C_{6-14})$aryl-$(C_{1-16})$alkyl-$N(R_3R_4)$, $(C_{1-16})$alkyl-$(C_{1-13})$heterocyclyl-$N(R_3R_4)$, $(C_{1-16})$alkyl-$(C_{1-13})$heterocyclyl-$(C_{1-16})$alkyl-$N(R_3R_4)$, carbonyl-$N(R_3R_4)$, $(C_{1-4})$alkyl-carbonyl-$N(R_3R_4)$, $(C_{2-16})$alkenyl-$N(R_3R_4)$,
$(C_{2-16})$alkenyl-$(C_{6-14})$aryl-$N(R_3R_4)$,
$(C_{2-16})$alkenyl-$(C_{6-14})$aryl-$(C_{1-16})$alkyl-$N(R_3R_4)$,
$(C_{2-16})$alkenyl-$(C_{1-13})$heterocyclyl-$N(R_3R_4)$,
$(C_{2-16})$alkenyl-$(C_{1-13})$heterocyclyl-$(C_{1-16})$alkyl-N $(R_3R_4)$, wherein heterocyclyl includes aliphatic and aromatic heterocyclyl comprising at least one heteroatom selected from N, O, S and wherein alkyl, aryl, heterocyclyl or alkenyl is optionally substituted comprising substituents which optionally having heteroatoms selected from O, N, S, halogen;

$R_3$ and $R_4$ independently of each other are
hydrogen,
$(C_{1-16})$alkyl,
$(C_{2-16})$alkenyl,
hydroxy$(C_{1-16})$alkyl,
amino-$(C_{1-16})$alkyl,
mono or di-$(C_{1-6})$alkylamino-$(C_{1-16})$alkyl,
guanidino$(C_{1-16})$alkyl, ureido$(C_{1-16})$alkyl or thioureido $(C_{1-16})$alkyl,
amino$(C_{1-6})$alkyl-$(C_{6-14})$aryl-$(C_{1-6})$alkyl,
amino$(C_{1-6})$alkyl-$(C_{6-14})$aryl,
guanidino$(C_{1-6})$alkyl-$(C_{6-14})$aryl-$(C_{1-6})$alkyl,
amino-$(C_{1-6})$alkyloxy-$(C_{1-6})$alkyl,
amino$(C_{3-8})$cycloalkyl,
amino$(C_{1-6})$alkyl-$(C_{3-8})$cycloalkyl,
amino$(C_{3-8})$cycloalkyl-$(C_{1-6})$alkyl,
amino$(C_{1-6})$alkyl-$(C_{3-8})$cycloalkyl-$(C_{1-6})$alkyl,
$(C_{1-13})$heterocyclyl-$(C_{1-16})$alkyl,
$(C_{6-14})$aryl-$(C_{1-16})$alkyl,
$(C_{1-13})$heterocyclyl,
amino-$(C_{6-14})$aryl-$(C_{1-16})$alkyl,
amino-$(C_{1-6})$alkyloxy-$(C_{6-14})$aryl-$(C_{1-6})$alkyl,
amino$(C_{1-6})$alkyl-$(C_{6-12})$aryl-carbonyl,
amino$(C_{1-6})$alkyl-amido-$(C_{6-12})$aryl$(C_{1-6})$alkyl,
$(C_{1-4})$alkylcarbonyl,
carbamimidoyl, carbamoyl, thiocarbamoyl, wherein heterocyclyl includes aliphatic and aromatic heterocyclyl comprising at least one heteroatom selected from N, O, S, and wherein alkyl, cycloalkyl, heterocyclyl, alkenyl or aryl is optionally further substituted, by
amino$(C_{1-4})$alkyl, amido, mono or di-$(C_{1-4})$alkyl-amido, $(C_{1-6})$alkyloxy-carbonyl, halogen, oxo, hydroxy X is sulfur or oxygen, in particular sulfur, and $R'_2$ is a hydrocarbon group comprising 1 to 22 carbon atoms, optionally comprising heteroatoms selected from N, O, S, halogen, in particular N or O, or a pharmaceutically acceptable salt, solvate, prodrug or metabolite thereof, wherein the naturally occurring pleuromutilin is of formula (PLEU)

PLEU

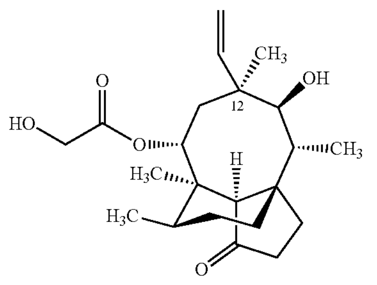

for the specific use in the treatment or prevention of a bacterial infection mediated by spirochetes, in particular a bacterial infection mediated by bacteria selected from the phylum of Spirochaetes, preferably the bacteria being selected from the order of Spirochaetales or Leptospirales, more preferably selected from the group consisting of the genera *Borrelia, Borreliella, Leptospira*, and *Treponema*.

The invention likewise provides a method of treatment or prevention of a bacterial infection comprising administering a compound according to the generic formula (VI) as defined above, or a pharmaceutically acceptable salt, solvate, ester of metabolite thereof to a subject in need of such treatment, wherein the bacterial infection is mediated by spirochetes or bacteria selected from the phylum of Spirochaetes as well as a use of the compound for the manufacture of a medicament for the specific treatment or prevention as defined above.

The above-mentioned embodiments and preferences with respect to diseases mediated by spirochetes analogously apply in the context of the compound according to the generic formula (VI) for this specific use or method.

Regarding the compound of generic formula (VI), in preferred embodiments, a) $R'_2$ is
$(C_{1-16})$alkyl,
$(C_{3-12})$cycloalkyl,
$(C_{1-13})$heterocyclyl,
$(C_{6-14})$aryl,
wherein heterocyclyl includes aliphatic and aromatic heterocyclyl comprising at least one heteroatom selected from N, O, S, and wherein alkyl, cycloalkyl, aryl, heterocyclyl is unsubstituted or substituted by substituents optionally having a heteroatom selected from O, N, S, and halogen.

b) $R'_2$ is
alkyl,
optionally substituted by
hydroxy or amino,
$(C_{3-12})$cycloalkyl wherein the cycloalkyl group is optionally further substituted by amino or amino $(C_{1-4})$alkyl wherein the amino or aminoalkyl group is optionally further substituted by amino $(C_{1-6})$alkylcarbonyl and optionally $(C_{1-4})$alkyl,
$(C_{2-11})$heterocyclyl, wherein a nitrogen in the ring as a heteroatom optionally is further substituted by amino$(C_{1-6})$alkylcarbonyl,
cycloalkyl,
optionally substituted by
amino$(C_{1-4})$alkyl, wherein the amino group is optionally further substituted by amino$(C_{1-6})$alkylcarbonyl,
hydroxy,
amino, wherein the amino group is optionally further substituted by amino$(C_{1-6})$alkylcarbonyl and optionally $(C_{1-4})$alkyl,
amino and hydroxy, wherein the amino group is optionally further substituted by amino$(C_{1-6})$alkylcarbonyl and optionally $(C_{1-4})$alkyl,
$(C_{1-4})$alkylamino, wherein alkyl is optionally further substituted by one or more halogen atoms;
aliphatic $(C_{2-11})$heterocyclyl,
comprising 1 to 4 heteroatoms selected from N, O, S, wherein a nitrogen in the ring as heteroatom is optionally further substituted by $(C_{1-4})$alkyl,
amino$(C_{1-6})$alkylcarbonyl,
aryl,
optionally substituted by
hydroxy, halogen, amino, hydroxy$(C_{1-4})$alkyl, bis-(hydroxy$(C_{1-4})$alkyl), amino$(C_{1-4})$alkyl, bis-(amino$(C_{1-4})$alkyl), wherein the amino group in amino$(C_{1-4})$alkyl optionally is further substituted,
aminocarbonyl, wherein the nitrogen optionally is substituted by
amino$(C_{1-12})$alkyl, bis-(amino$(C_{1-12})$alkyl), hydroxy $(C_{1-6})$alkyl, bis-(hydroxy$(C_{1-6})$alkyl) or diamino $(C_{1-6})$alkyl,
$(C_{1-12})$alkyl, which alkyl optionally is substituted by
amino, which amino optionally is acylated, particularly amino is substituted by formyl, $(C_{1-4})$alkylcarbonyl, saturated or unsaturated heterocyclyl comprising 1 to 3 heteroatoms, particularly N, and 4 to 8, particularly 5 to 6 ring members, $(C_{6-14})$ aryl, particularly phenyl, which aryl optionally is substituted by amino$(C_{1-4})$alkyl,
or
the nitrogen of the aminocarbonyl group is part of $(C_{3-8})$heterocyclyl, including aliphatic and aromatic heterocyclyl, comprising one or more heteroatoms selected from N, O, S preferably N, wherein the heterocycle is optionally further substituted by amino$(C_{1-4})$alkyl;
$(C_{1-6})$alkyl, which $(C_{1-6})$alkyl group is optionally substituted by aminocarbonyl, wherein the nitrogen of the aminocarbonyl group is optionally further substituted by amino$(C_{1-12})$alkyl, diamino-$(C_{1-12})$alkyl, bis-(amino$(C_{1-12})$alkyl), hydroxy $(C_{1-6})$alkyl, bis-(hydroxy$(C_{1-6})$alkyl),
acylated amino$(C_{1-4})$alkyl,
aromatic $(C_{1-13})$heterocyclyl, comprising 1 to 4 heteroatoms,
wherein the aromatic heterocyclyl is optionally substituted by $(C_{1-6})$alkyl, amino or hydroxy wherein the alkyl group is optionally further substituted by halogen or amino or the aromatic heterocyclyl is optionally substituted by aminocarbonyl wherein the amino group is optionally further substituted by amino$(C_{1-12})$alkyl, bis-(amino$(C_{1-12})$alkyl), hydroxy$(C_{1-6})$alkyl, bis-(hydroxy$(C_{1-6})$alkyl) or diamino$(C_{1-6})$alkyl.

c) R'2 is amido-phenyl, amido(C1-4)alkyl-phenyl, wherein the nitrogen of the amido group is unsubstituted or substituted by amino(C1-8)alkyl, in which alkyl optionally is further substituted.

d) R'2 is
amino$(C_{3-12})$cycloalkyl,
amino$(C_{1-4})$alkyl$(C_{3-12})$cycloalkyl,
amino$(C_{3-12})$cycloalkyl$(C_{1-4})$alkyl, or
amino$(C_{1-4})$alkyl$(C_{3-12})$cycloalkyl$(C_{1-4})$alkyl,
wherein the amino group is unsubstituted or substituted by amino$(C_{1-6})$alkylcarbonyl, or amino$(C_{1-6})$alkylcarbonyl and $(C_{1-4})$alkyl.

e) $R'_2$ is $(C_{2-11})$heterocyclyl comprising 1 to 4 heteroatoms selected from N, O, S, wherein, if a nitrogen in the ring as a heteroatom is present, said nitrogen is unsubstituted or optionally further substituted by
$(C_{1-4})$alkyl,
amino$(C_{1-6})$alkylcarbonyl.

f) X is S,
$R'_1$ is as defined above and $R'_2$ is aminoethyl-amidomethyl-phenyl, aminopropyl-amidomethyl-phenyl, hydroxyphenyl-(amino)ethyl-amidomethyl-phenyl, aminomethyl-phenyl-(amino)ethyl-amidomethyl-phenyl, aminopropyl-amidophenyl, aminomethyl-phenylmethyl-amido-phenyl, aminomethyl-phenyl, aminoacetyl-aminomethyl-phenyl, bis(aminomethyl)phenyl, bisaminopropyl-amidomethyl-phenyl, (2-amino)-aminopropyl-amidomethyl-phenyl, aminoethyl-aminomethyl-phenyl, aminopropyl-aminomethyl-phenyl, allyl-aminomethyl-phenyl, aminomethyl-phenylmethyl-aminomethyl-phenyl, hydroxymethyl-phenyl, bis(hydroxymethyl)-phenyl, (tetrafluoro-hydroxymethyl)-phenyl, amino-hydroxy-cyclohexyl, hydroxyethyl, aminoethyl, piperazinocarbonyl-phenyl, aminomethyl-piperidine-carbonyl-phenyl, piperidine-ylmethyl-amido-phenyl, pyridine-ylmethyl-amido-phenyl, acetyl-aminopropyl-amido-phenyl, formyl-aminopropyl-amido-phenyl, amido-phenyl, aminohexyl-amidophenyl, aminoethyl-amidophenyl, (5-Amino)-4H-[1,2,4]triazol-3-yl, pyridinyl, hydroxyphenyl, fluorophenyl, purinyl, aminophenyl, acetyl-aminomethyl-phenyl, cyclopropyl-aminomethyl-phenyl, aminopropyl-amidopyridinyl, hydroxypropyl-amidophenyl, amino-purinyl, difluoroethylamino-cyclohexyl, amino-hydroxy-cyclohexyl, azepanyl, aminomethyl-cyclohexylmethyl, N-methyl-piperidinyl, piperidinyl, aminomethylcyclohexyl, aminopropylphenyl, phenyl, N-aminomethylcarbonyl-piperidinyl, N-aminoethylcarbonyl-piperidinyl, N-aminomethyl-carbonyl-piperidinylmethyl, aminomethylamidomethylcyclohexyl, aminomethyl-pyridinyl, aminomethylamidocyclohexyl.

g) the compound is of formula (VII)

(VII)

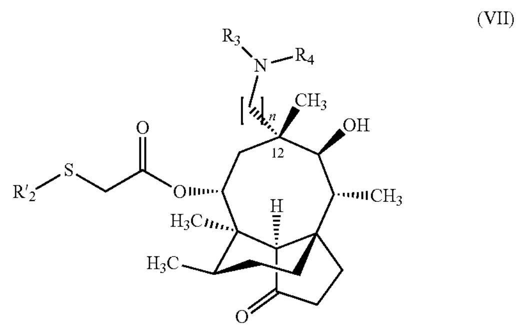

wherein $R'_2$ is as defined above,
n is 1 to 12
$R_3$ is H, aminoethyl, aminopropyl, aminobutyl, aminopentyl, aminohexyl, aminooctyl, aminodecyl, dimethylaminopropyl, dimethylamidopentyl, guanidinobutyl, guanidinohexyl, carbamimidoyl, aminomethylcyclohexylmethyl, aminopropoxypropyl, aminocyclohexyl, hydroxyhexyl, dihydroxypropyl, aminomethylphenylmethyl, guanidinomethylphenylmethyl, phenylmethyl, morpholinopropyl, piperidinyl, hexyl, pyridinylethyl, allyl, amido-benzyl, aminopropyl-amidobenzyl, (2-amino)-amidoethyl-benzyl, (2-amino)-dimethylamidoethyl-benzyl, 2-amino-1-aminomethyl-ethyl, 5-amino-5-ethoxycarbonyl-pentyl, aminomethylphenylpropyl, aminomethylphenyl, aminophenymethyl, aminoethoxyphenylmethyl, aminomethyl-fluorophenyl-methyl, aminomethyl-difluorophenyl-methyl, and
$R_4$ is H, $(C_{1-4})$alkylcarbonyl or aminomethylphenylcarbonyl.

h) $R'_2$ is as defined above and
$R'_1$ is aminomethylphenylpropyl, aminoethylaminomethylphenylethenyl, aminoethylaminomethylphenylethyl, aminomethylphenylethyl, aminomethylphenylethyl, pyridinylethenyl, aminoethylaminofluorophenylethenyl.

i) the compound is selected from the group consisting of
12-epi-12-desvinyl-14-O-{{4-[(3-Amino-propylcarbamoyl)-methyl]-phenylsulfanyl}-acetyl}-12-[(3-amino-propylamino)-methyl] mutilin,
12-epi-12-desvinyl-14-O-{{4-[(2-Amino-ethylcarbamoyl)-methyl]-phenylsulfanyl}-acetyl}-12-[(3-amino-propylamino)-methyl] mutilin,
12-epi-12-desvinyl-14-O-{{4-([Bis-(3-amino-propyl)-carbamoyl]-methyl}-phenylsulfanyl)-acetyl}-12-[(3-amino-propylamino)-methyl] mutilin,
12-epi-12-desvinyl-14-O-{{4-[(2,3-Diamino-propylcarbamoyl)-methyl]-phenylsulfanyl}-acetyl}-12-[(3-amino-propylamino)-methyl] mutilin,
12-epi-12-desvinyl-14-O-{{4-[(2-Amino-ethylcarbamoyl)-methyl]-phenylsulfanyl}-acetyl}-12-[(2-amino-ethyl-amino)-methyl] mutilin,
12-epi-12-desvinyl-14-O-{{4-[(3-Amino-propylcarbamoyl)-methyl]-phenylsulfanyl}-acetyl}-12-[(2-amino-ethylamino)-methyl] mutilin,
12-epi-12-desvinyl-14-O-{{4-[(3-Amino-propylcarbamoyl)-methyl]-phenylsulfanyl}-acetyl}-12-[(4-amino-butylamino)-methyl] mutilin,
12-epi-12-desvinyl-14-O-{{4-[(3-Amino-propylcarbamoyl)-methyl]-phenylsulfanyl}-acetyl}-12-[(5-amino-pentylamino)-methyl] mutilin,
12-epi-12-desvinyl-14-O-{{4-[(3-Amino-propylcarbamoyl)-methyl]-phenylsulfanyl}-acetyl}-12-[(4-aminomethyl-benzylamino)-methyl] mutilin,
12-epi-12-desvinyl-14-O-{{4-[(3-Amino-propylcarbamoyl)-methyl]-phenylsulfanyl}-acetyl}-12-[(6-amino-hexylamino)-methyl] mutilin,
12-epi-12-desvinyl-14-O-{{4-[(3-Amino-propylcarbamoyl)-methyl]-phenylsulfanyl}-acetyl}-12-[(6-guanidino-hexylamino)-methyl] mutilin,
12-epi-12-desvinyl-14-O-{{4-[(3-Amino-propylcarbamoyl)-methyl]-phenylsulfanyl}-acetyl}-12-[(4-guanidino-butylamino)-methyl] mutilin,
12-epi-12-desvinyl-14-O-{{4-[(3-Amino-propylcarbamoyl)-methyl]-phenylsulfanyl}-acetyl}-12-[(allylamino)-methyl] mutilin,
12-epi-12-desvinyl-14-O-{{4-[(3-Amino-propylcarbamoyl)-methyl]-phenylsulfanyl}-acetyl}-12-aminomethyl mutilin,
12-epi-12-desvinyl-14-O-{{4-[(3-Amino-propylcarbamoyl)-methyl]-phenylsulfanyl}-acetyl}-12-[(benzylamino)-methyl] mutilin,
12-epi-12-desvinyl-14-O-{{4-[(3-Amino-propylcarbamoyl)-methyl]-phenylsulfanyl}-acetyl}-12-[(4-guanidinomethyl-benzylamino)-methyl] mutilin,
12-epi-12-desvinyl-14-O-{{4-[(3-Amino-propylcarbamoyl)-methyl]-phenylsulfanyl}-acetyl}-12-[(6-hydroxy-hexylamino)-methyl] mutilin,
12-epi-12-desvinyl-14-O-{{4-[(3-Amino-propylcarbamoyl)-methyl]-phenylsulfanyl}-acetyl}-12-[(2,3-dihydroxypropylamino)-methyl] mutilin,
12-epi-12-desvinyl-14-O-{{4-[(3-Amino-propylcarbamoyl)-methyl]-phenylsulfanyl}-acetyl}-12-[(4-piperidylamino)-methyl] mutilin,
12-epi-12-desvinyl-14-O-{{4-[(3-Amino-propylcarbamoyl)-methyl]-phenylsulfanyl}-acetyl}-12-[(3-morpholin-4-yl-propylamino)-methyl] mutilin,
12-epi-12-desvinyl-14-O-{{4-[(3-Amino-propylcarbamoyl)-methyl]-phenylsulfanyl}-acetyl}-12-[(3-dimethyl-amino-propylamino)-methyl] mutilin,
12-epi-12-desvinyl-14-O-{{4-[(3-Amino-propylcarbamoyl)-methyl]-phenylsulfanyl}-acetyl}-12-[(S)-5-amino-5-ethoxycarbonyl-pentylamino-methyl] mutilin,
12-epi-12-desvinyl-14-O-{[4-(4-Aminomethyl-benzylcarbamoyl)-phenylsulfanyl]-acetyl}-12-[(6-amino-hexylamino)-methyl] mutilin,
12-epi-12-desvinyl-14-O-{[4-(4-Aminomethylbenzylcarbamoyl)-phenylsulfanyl]-acetyl}-12-[(6-guanidino-hexylamino)-methyl] mutilin,
12-epi-12-desvinyl-14-O-{[(4-Piperazinylcarbamoyl)-phenylsulfanyl]-acetyl}-12-[(6-guanidino-hexylamino)-methyl] mutilin,
12-epi-12-desvinyl-14-O-{[4-(4-Aminomethyl-piperidine-1-carbonyl)-phenylsulfanyl]-acetyl}-12-[(6-guanidino-hexylamino)-methyl] mutilin,
12-epi-12-desvinyl-14-O-{(4-[(Piperidin-4-ylmethyl)-carbamoyl]-phenylsulfanyl)-acetyl}-12-[(6-guanidino-hexylamino)-methyl] mutilin,
12-epi-12-desvinyl-14-O-{(4-[(Pyridin-4-ylmethyl)-carbamoyl]-phenylsulfanyl)-acetyl}-12-[(6-amino-hexylamino)-methyl] mutilin,
12-epi-12-desvinyl-14-O-{[3-(3-Aminopropylcarbamoyl)-phenylsulfanyl]-acetyl}-12-[(6-guanidino-hexylamino)-methyl] mutilin,
12-epi-12-desvinyl-14-O-{[4-(3-Acetylamino-propylcarbamoyl)-phenylsulfanyl]-acetyl}-12-[(3-amino-propylamino)-methyl] mutilin,
12-epi-12-desvinyl-14-O-{[4-(3-Formylamino-propylcarbamoyl)-phenylsulfanyl]-acetyl}-12-[(3-amino-propylamino)-methyl] mutilin,
12-epi-12-desvinyl-14-O-{[4-(3-Amino-propylcarbamoyl)-phenylsulfanyl]-acetyl}-12-[(3-amino-propylamino)-methyl] mutilin,
12-epi-12-desvinyl-14-O-{(4-[(3-Aminopropylcarbamoyl)-phenylsulfanyl)-acetyl}-12-[(4-aminomethyl-benzylamino)-methyl] mutilin,
12-epi-12-desvinyl-14-O-{(4-[(3-Aminopropylcarbamoyl)-phenylsulfanyl)-acetyl}-12-[(6-amino-hexylamino)-methyl] mutilin,
12-epi-12-desvinyl-14-O-{[4-(3-Aminopropylcarbamoyl)-phenylsulfanyl]-acetyl}-12-[(6-guanidino-hexylamino)-methyl] mutilin,
12-epi-12-desvinyl-14-O-{[4-(3-Aminopropylcarbamoyl)-phenylsulfanyl]-acetyl}-12-[(8-amino-octylamino)-methyl] mutilin,
12-epi-12-desvinyl-14-O-{[4-(3-Aminopropylcarbamoyl)-phenylsulfanyl]-acetyl}-12-[(10-amino-decylamino)-methyl] mutilin,
12-epi-12-desvinyl-14-O-{(4-Carbamoyl-phenylsulfanyl)-acetyl}-12-[(6-guanidino-hexylamino)-methyl] mutilin,
12-epi-12-desvinyl-14-O-{[4-(3-Amino-propylcarbamoyl)-phenylsulfanyl]-acetyl}-12-{[3-(3-amino-propoxy)-propylamino)]-methyl} mutilin,
12-epi-12-desvinyl-14-O-{[4-(3-Amino-propylcarbamoyl)-phenylsulfanyl]-acetyl}-12[(2-pyridin-4-yl-ethylamino)-methyl] mutilin,
12-epi-12-desvinyl-14-O-{[4-(6-Amino-hexylcarbamoyl)-phenylsulfanyl]-acetyl}-12-[(6-guanidino-hexylamino)-methyl] mutilin,
12-epi-12-desvinyl-14-O-{[4-(2-Amino-ethylcarbamoyl)-phenylsulfanyl]-acetyl}-12-[(6-guanidino-hexylamino)-methyl] mutilin, 12-epi-12-desvinyl-14-O-{[4-(3-Aminopropylcarbamoyl)-phenylsulfanyl]-acetyl}-12-{[3-(4-aminomethyl-phenyl)-propylamino]-methyl} mutilin,
12-epi-12-desvinyl-14-O-{[(4-Aminomethyl-cyclohexyl)-methylsulfanyl]-acetyl}-12-[(6-amino-hexylamino)-methyl] mutilin,
12-epi-14-O-[(1-Methyl-piperidin-4-ylsulfanyl)-acetyl}-12-[(6-guanidino-hexylamino)-methyl] mutilin,
12-epi-14-O-[(Piperidin-4-ylsulfanyl)-acetyl]-12-[(6-amino-hexylamino)-methyl] mutilin,
12-epi-12-desvinyl-14-O-{[(4-Aminomethyl-cyclohexyl)-sulfanyl]-acetyl}-12-[(6-amino-hexylamino)-methyl] mutilin,
12-epi-12-desvinyl-14-O-{[4-(3-Amino-propyl)-phenylsulfanyl]-acetyl}-12-[(6-amino-hexylamino)-methyl] mutilin,
12-epi-12-desvinyl-14-O-{(4-[(3-Amino-propylcarbamoyl)-methyl]-phenylsulfanyl)-acetyl}-12-{[(3-amino-propyl)-acetylamino]-methyl} mutilin,
12-epi-12-desvinyl-14-O-{(4-[(3-Amino-propylcarbamoyl)-methyl]-phenylsulfanyl)-acetyl}-12-(3-amino-propylcarbamoyl) mutilin,
12-epi-12-desvinyl-14-O-{[4-(3-Amino-propylcarbamoyl)-phenylsulfanyl]-acetyl}-12-(4-aminomethyl-benzylcarbamoyl) mutilin,
12-epi-12-desvinyl-14-O-{{4-[(3-Amino-propylcarbamoyl)-methyl]-phenylsulfanyl}-acetyl}-12-[2-(3-amino-propylamino)-ethyl] mutilin,
12-epi-12-desvinyl-14-O-[(3-Hydroxymethyl-phenylsulfanyl)-acetyl]-12-[(3-amino-propylamino)-methyl] mutilin,
12-epi-12-desvinyl-14-O-[(3-Hydroxymethyl-phenylsulfanyl)-acetyl]-12-[(6-amino-hexylamino)-methyl] mutilin,
12-epi-12-desvinyl-14-O-[(3-Hydroxymethyl-phenylsulfanyl)-acetyl]-12-[(4-aminomethyl-benzylamino)-methyl] mutilin,
12-epi-12-desvinyl-14-O-[(3-Hydroxymethyl-phenylsulfanyl)-acetyl]-12-[(6-guanidino-hexylamino)-methyl] mutilin,
12-epi-12-desvinyl-14-O-[(4-Hydroxymethyl-phenylsulfanyl)-acetyl]-12-[(3-amino-propylamino)-methyl] mutilin,
12-epi-12-desvinyl-14-O-[(4-Hydroxymethyl-phenylsulfanyl)-acetyl]-12-[(4-aminomethyl-benzylamino)-methyl] mutilin,
12-epi-12-desvinyl-14-O-[(4-Hydroxymethyl-phenylsulfanyl)-acetyl]-12-[(6-amino-hexylamino)-methyl] mutilin,
12-epi-12-desvinyl-14-O-[(3,5-Bis-hydroxymethyl-phenylsulfanyl)-acetyl]-12-[(3-amino-propylamino)-methyl] mutilin,
12-epi-12-desvinyl-14-O-{[(2,3,5,6-Tetrafluoro-4-hydroxymethyl)-phenylsulfanyl]-acetyl}-12-[(4-aminomethyl-benzylamino)-methyl]-mutilin,
12-epi-12-desvinyl-14-O-{[(1R,2R,4R)-4-Amino-2-hydroxy-cyclohexylsulfanyl]-acetyl}-12-[(3-amino-propylamino)-methyl] mutilin,
12-epi-12-desvinyl-14-O-{[(1R,2R,4R)-4-Amino-2-hydroxy-cyclohexylsulfanyl]-acetyl}-12-[(4-aminomethyl-benzylamino)-methyl] mutilin,
12-epi-12-desvinyl-14-O-[(2-Hydroxy-ethylsulfanyl)-acetyl]-12-[(4-aminomethyl-benzylamino)-methyl] mutilin,
12-epi-12-desvinyl-14-O-[(2-Amino-ethylsulfanyl)-acetyl]-12-[(4-aminomethyl-benzylamino)-methyl] mutilin,
12-epi-12-desvinyl-14-O-{[(5-Amino-4H-1,2,4-triazol-3-yl)-sulfanyl]-acetyl}-12-[(6-amino-hexylamino)-methyl] mutilin,
12-epi-12-desvinyl-14-O-[(2-Amino-ethylsulfanyl)-acetyl]-12-[(6-amino-hexylamino)-methyl] mutilin,
12-epi-12-desvinyl-14-O-[(Pyridin-4-ylsulfanyl)-acetyl]-12-[(6-amino-hexylamino)-methyl] mutilin,
12-epi-12-desvinyl-14-O-[(Pyridin-4-ylsulfanyl)-acetyl]-12-[(6-guanidino-hexylamino)-methyl] mutilin,
12-epi-12-desvinyl-14-O-[(3-Hydroxy-phenylsulfanyl)-acetyl]-12-[(6-amino-hexylamino)-methyl] mutilin,
12-epi-12-desvinyl-14-O-[(4-Fluoro-phenylsulfanyl)-acetyl]-12-[(6-amino-hexylamino)-methyl] mutilin,
12-epi-12-desvinyl-14-O-{[(7H-Purin-6-yl)-sulfanyl]-acetyl}-12-[(6-amino-hexylamino)-methyl] mutilin,
12-epi-12-desvinyl-14-O-[(3-Amino-phenylsulfanyl)-acetyl]-12-[(3-amino-propylamino)-methyl] mutilin,
12-epi-12-desvinyl-14-O-(Phenylsulfanyl-acetyl)-12-[(4-aminomethyl-benzylamino)-methyl] mutilin,
12-epi-12-desvinyl-14-O-[(4-Fluoro-phenylsulfanyl)-acetyl]-12-[(4-aminomethyl-benzylamino)-methyl] mutilin,
12-epi-12-desvinyl-14-O-[(Pyridin-2-ylsulfanyl)-acetyl]-12-[(4-aminomethyl-benzylamino)-methyl] mutilin,
12-epi-12-desvinyl-14-O-[(Pyridin-4-ylsulfanyl)-acetyl]-12-[(4-aminomethyl-benzylamino)-methyl] mutilin,
12-epi-12-desvinyl-14-O-{[1-(2-Amino-acetyl)-piperidin-4-yl-sulfanyl)]-acetyl}-12-[(4-aminomethyl-benzylamino)-methyl] mutilin,
12-epi-12-desvinyl-14-O-{[1-(3-Amino-propionyl)-piperidin-4-yl-sulfanyl)]-acetyl}-12-[(4-aminomethyl-benzylamino)-methyl] mutilin,
12-epi-12-desvinyl-14-O-{[1-(3-Amino-propionyl)-piperidin-4-yl-sulfanyl]-acetyl}-12-[(6-amino-hexylamino)-methyl] mutilin,
12-epi-12-desvinyl-14-O-{[1-(2-Amino-acetyl)-piperidin-4-yl-methylsulfanyl]-acetyl}-12-[(4-aminomethyl-phenylamino)-methyl] mutilin,
12-epi-12-desvinyl-14-O-{[1-(2-Amino-acetyl)-piperidin-4-yl-methylsulfanyl]-acetyl}-12-[(4-amino-benzylamino)-methyl] mutilin,
12-epi-12-desvinyl-14-O-{[1-(2-Amino-acetyl)-piperidin-4-yl-sulfanyl]-acetyl}-12{2-[4-(2-amino-ethoxy)-benzylamino]-methyl} mutilin,
12-epi-12-desvinyl-14-O-{{4-[(2-Amino-acetylamino)-methyl]-cyclohexylsulfanyl}-acetyl}-12-[{4-[(2-amino-ethoxy)-benzylamino]-methyl} mutilin,
12-epi-12-desvinyl-14-O-[(4-Aminomethyl-phenylsulfanyl)-acetyl]-12-[(3-amino-propylamino)-methyl] mutilin,
12-epi-12-desvinyl-14-O-[(3-Aminomethyl-phenylsulfanyl)-acetyl]-12-[(3-amino-propylamino)-methyl] mutilin,
12-epi-12-desvinyl-14-O-[(3-Aminomethyl-phenylsulfanyl)-acetyl]-12-[(6-guanidino-hexylamino)-methyl] mutilin,
12-epi-12-desvinyl-14-O-[(4-Aminomethyl-phenylsulfanyl)-acetyl]-12-[(4-aminomethyl-benzylamino)-methyl] mutilin,
12-epi-12-desvinyl-14-O-[(4-Aminomethyl-phenylsulfanyl)-acetyl]-12-[(6-amino-hexylamino)-methyl] mutilin,
12-epi-12-desvinyl-14-O-[(3-Aminomethyl-phenylsulfanyl)-acetyl]-12-[((4-aminomethyl-cyclohexyl)-methylamino)-methyl] mutilin,
12-epi-12-desvinyl-14-O-[(4-Aminomethyl-phenylsulfanyl)-acetyl]-12-{[(4-aminocyclohexyl)-amino]-methyl} mutilin,
12-epi-12-desvinyl-14-O-[(4-Aminomethyl-phenylsulfanyl)-acetyl]-12-[(hexylamino)-methyl] mutilin,
12-epi-12-desvinyl-14-O-[(4-Aminomethyl-phenylsulfanyl)-acetyl]-12-[(4-carbamoylphenyl)-methylamino)-methyl] mutilin, 12-epi-12-desvinyl-14-O-[(4-Aminomethyl-phenylsulfanyl)-acetyl]-12-{[4-(3-amino-propylcarbamoyl)-benzylamino]-methyl} mutilin, 12-epi-12-desvinyl-14-O-[(4-Aminomethyl-phenylsulfanyl)-acetyl]-12-[(5-dimethylcarbamoyl-pentylamino)-methyl] mutilin, 12-epi-12-desvinyl-14-O-[(4-Aminomethyl-phenylsulfanyl)-acetyl]-12-{[4-(2-amino-2-carbamoyl-ethyl)-benzylamino]-methyl} mutilin, 12-epi-12-desvinyl-14-O-[(4-Aminomethyl-phenylsulfanyl)-acetyl]-12-{[4-(2-amino-2-dimethylcarbamoyl-ethyl)-benzylamino]-methyl} mutilin, 12-epi-12-desvinyl-14-O-{[5-Aminomethyl-pyridin-2-yl-sulfanyl)]-acetyl}-12-[(4-aminomethyl-benzylamino)-methyl] mutilin, 12-epi-12-Desvinyl-14-O-{[5-aminomethyl-pyridin-2-yl-sulfanyl)]-acetyl}-12-[(4-aminomethyl-3-fluoro-benzylamino)-methyl] mutilin, 12-epi-12-desvinyl-14-O-{[(4-Aminomethyl-cyclohexyl)-methylsulfanyl)-acetyl]{[(4-Aminomethyl-cyclohexyl)-methylsulfanyl]-acetyl}-12-[(4-aminomethyl-benzylamino)-methyl] mutilin, 12-epi-12-desvinyl-14-O-{1-(2-Amino-acetyl)-piperidin-4-yl-sulfanyl]-acetyl}-12-[(4-aminomethyl-3-fluoro-benzylamino)-methyl] mutilin, 12-epi-12-Desvinyl-14-O-{{4-[(2-Amino-acetylamino)-methyl]-cyclohexylsulfanyl}-acetyl}-12-[(4-aminomethyl-3-fluoro-benzylamino)-methyl] mutilin, 12-epi-12-desvinyl-14-O-{[5-Aminomethyl-pyridin-2-yl-sulfanyl]-acetyl}-12-[(4-aminomethyl-2,5-difluoro-benzylamino)-methyl] mutilin, 12-epi-12-desvinyl-14-O-[(4-Aminomethyl-phenylsulfanyl)-acetyl]-12-[(2-amino-1-aminomethyl-ethylamino)-methyl] mutilin, 12-epi-12-Desvinyl-14-O-[(5-aminomethyl-pyridin-2-yl-sulfanyl)-acetyl]-12-[(6-amino-hexylamino)-methyl] mutilin, 12-epi-12-desvinyl-14-O-{(4-[(2-Amino-acetylamino)-methyl]-phenylsulfanyl)-acetyl}-12-[(3-amino-propylamino)-methyl] mutilin, 12-epi-12-desvinyl-14-O-{(4-[(2-Amino-3-(4-hydroxy-phenyl)-propionylamino)-methyl]-phenylsulfanyl)-acetyl}-12-[(3-amino-propylamino)-methyl] mutilin, 12-epi-12-desvinyl-14-O-{(4-[(3-Amino-propionylamino)-methyl]-phenylsulfanyl)-acetyl}-12-[(3-amino-propylamino)-methyl] mutilin, 12-epi-12-desvinyl-14-O-{(4-[(2-Amino-acetylamino)-methyl]-phenylsulfanyl)-acetyl}-12-[4-aminomethyl-benzylamino-methyl] mutilin, 12-epi-12-desvinyl-14-O-{(4-[(2-Amino-acetylamino)-methyl]-phenylsulfanyl)-acetyl}-12-(6-amino-hexylamino-methyl) mutilin, 12-epi-12-desvinyl-14-O-{[(3-Acetylamino-methyl)-phenylsulfanyl]-acetyl}-12-[(3-amino-propylamino)-methyl] mutilin, 12-epi-12-desvinyl-14-O-{(4-{[2-Amino-3-(4-aminomethyl-phenyl)-propionylamino]-methyl}-phenylsulfanyl)-acetyl}-12-[(3-amino-propylamino)-methyl] mutilin, 12-epi-12-desvinyl-14-O-{{4-[(3-Amino-propylamino)-methyl]-phenylsulfanyl}-acetyl}-12-[(3-amino-propylamino)-methyl] mutilin, 12-epi-12-desvinyl-14-O-{{3-[(3-Amino-propylamino)-methyl]-phenylsulfanyl}-acetyl}-12-[(3-amino-propylamino)-methyl] mutilin, 12-epi-12-desvinyl-14-O-{{4-[(4-Aminomethyl-benzylamino)-methyl]-phenylsulfanyl}-acetyl}-12-[(3-amino-propylamino)-methyl] mutilin, 12-epi-12-desvinyl-14-O-[(3-Allylaminomethyl-phenylsulfanyl)-acetyl]-12-[(3-amino-propylamino)-methyl] mutilin, 12-epi-12-desvinyl-14-O-{{4-[(3-Amino-propylamino)-methyl]-phenylsulfanyl}-acetyl}-12-{[3-(3-amino-propoxy)-propylamino]-methyl} mutilin, 12-epi-12-desvinyl-14-O-[(4-Cyclopropylaminomethyl-phenylsulfanyl)-acetyl]-12-[(3-amino-propylamino)-methyl] mutilin, 12-epi-12-desvinyl-14-O-[(4-Cyclopropylaminomethyl-phenylsulfanyl)-acetyl]-12-[(6-amino-hexylamino)-methyl] mutilin, 12-epi-12-desvinyl-14-O-{{4-[(4-Aminomethyl-benzylamino)-methyl]-phenylsulfanyl}-acetyl}-12-[(6-amino-hexylamino)-methyl] mutilin, 12-epi-12-desvinyl-14-O-{{4-[(4-Aminomethyl-benzylamino)-methyl]-phenylsulfanyl}-acetyl}-12-[(4-aminomethyl-benzylamino)-methyl]-mutilin, 12-epi-12-desvinyl-14-O-[5-(3-Amino-propylcarbamoyl)-pyridin-2-ylsulfanyl]-acetyl-12-[(6-amino-hexylamino)-methyl] mutilin, 12-epi-12-desvinyl-14-O-[(2,5-Bis-aminomethyl-phenylsulfanyl)-acetyl]-12-[(3-amino-propy lamino)-methyl] mutilin, 12-epi-12-desvinyl-14-O-[(3,5-Bis-aminomethyl-phenylsulfanyl)-acetyl]-12-[(3-amino-propylamino)-methyl] mutilin, 12-epi-12-desvinyl-14-O-{[(3-Amino-propylcarbamoyl)-phenylsulfanyl]-acetyl}-12-[(2-guanidino-ethyl] mutilin, 12-epi-12-desvinyl-14-O-{[4-(3-Hydroxy-propylcarbamoyl)-phenylsulfanyl]-acetyl}-12-[(6-amino-hexylamino)-methyl] mutilin, 12-epi-12-desvinyl-14-O-[(2-Hydroxy-ethylsulfanyl)-acetyl]-12-[(6-amino-hexylamino)-methyl] mutilin, 12-epi-12-desvinyl-14-O-{[3-(2,2-Difluoro-ethylamino)-cyclohexylsulfanyl]-acetyl}-12-[(6-amino-hexylamino)-methyl] mutilin, 12-epi-12-desvinyl-14-O-[(2-Amino-7H-purin-6-ylsulfanyl)-acetyl]-12-[(6-amino-hexylamino)-methyl] mutilin, 12-epi-12-desvinyl-14-O-[(Azepan-4-ylsulfanyl)-acetyl]-12-[(6-amino-hexylamino)-methyl] mutilin, 12-epi-12-desvinyl-14-O-[(Azepan-4-ylsulfanyl)-acetyl]-12-[(6-guanidino-hexylamino)-methyl] mutilin, 12-epi-12-desvinyl-14-O-[(Azepan-4-ylsulfanyl)-acetyl]-12-[(4-aminomethyl-benzylamino)-methyl] mutilin, 12-epi-12-desvinyl-14-O-[(Azepan-4-ylsulfanyl)-acetyl]-12-[(6-amino-octylamino)-methyl] mutilin, 12-epi-12-desvinyl-14-O-{[1-(2-Amino-acetyl)-piperidin-4-yl-sulfanyl)]-acetyl}-12-[(6-amino-hexylamino)-ethyl] mutilin, 12-epi-12-desvinyl-14-O-{[1-(2-Amino-acetyl)-piperidin-4-yl-sulfanyl)]-acetyl}-12-[(4-aminomethyl-benzylamino)-ethyl] mutilin, 12-epi-12-desvinyl-14-O-[5-Hydroxymethyl-pyridin-2-yl-sulfanylacetyl]-12-[(4-aminomethyl-3-fluoro-benzylamino)-ethyl] mutilin, 12-epi-12-desvinyl-14-O-{4-[(2-Amino-acetylamino)-cyclohexylsulfanyl]-acetyl}-12-[(4-aminomethyl-3-fluoro-benzylamino)-ethyl] mutilin, 12-epi-12-desvinyl-14-O-{[1-(2-Amino-acetyl)-piperidin-4-yl-sulfanyl]-acetyl}-12-[(4-aminomethyl-3-fluoro-benzylamino)-ethyl] mutilin, 12-epi-12-desvinyl-14-O-[(5-Aminomethyl-pyridin-2-yl-sulfanyl)-acetyl]-12-[(4-aminomethyl-2,5-difluoro-benzylamino)-ethyl] mutilin, 12-epi-12-desvinyl-14-O-{[1-(2-Amino-acetyl)-piperidin-4-yl-sulfanyl]-acetyl}-12-[(4-aminomethyl-2,5-difluoro-benzylamino)-ethyl] mutilin, 12-epi-12-desvinyl-14-O-{[1-(2-Amino-acetyl)-piperidin-4-yl-sulfanyl]-acetyl}-12{2-[4-(2-amino-ethoxy)-benzylamino]-ethyl} mutilin, 12-epi-12-desvinyl-14-O-{{4-[(2-Amino-acetylamino)-methyl]-cyclohexylsulfanyl}-acetyl}-12-[(4-aminomethyl-3-fluoro-benzylamino)-ethyl] mutilin, 12-epi-12-desvinyl-14-O-[(Azepan-4-ylsulfanyl)-acetyl]-12-[(4-aminomethyl-phenylamino)-ethyl] mutilin, 12-epi-12-desvinyl-14-O-{{4-[(2-Amino-acetylamino)]-cyclohexylsulfanyl}-acetyl}-12-[(4-aminomethyl-phenylamino)-ethyl] mutilin, 12-epi-12-desvinyl-14-O-{[1-(2-Amino-acetyl)-piperidin-4-yl-methylsulfanyl]-acetyl}-12-[(4-aminomethyl-phenylamino)-ethyl] mutilin, 12-epi-12-desvinyl-14-O-{[1-(2-Amino-acetyl)-piperidin-4-yl-sulfanyl]-acetyl}-12-(8-amino-octyl) mutilin, 12-epi-12-desvinyl-14-O-{[1-(2-Amino-acetyl)-piperidin-4-yl-sulfanyl]-acetyl}-12-[3-(4-aminomethyl-phenyl)-propyl] mutilin, 12-epi-12-desvinyl-14-O-[(Azepan-4-yl-sulfanyl)-acetyl]-12-[3-(4-aminomethyl-phenyl)-propyl] mutilin, 12-epi-12-desvinyl-14-O-[(Azepan-4-yl-sulfanyl)-acetyl]-12-(6-amino-hexyl) mutilin, 12-epi-12-desvinyl-14-O-[(Azepan-4-yl-sulfanyl)-acetyl]-12-(8-amino-octyl) mutilin,)

12-epi-12-desvinyl-14-O-{{4-[(2-Amino-acetylamino)-methyl]-cyclohexylsulfanyl}-acetyl}-12-[2-{4-[(2-amino-ethylamino)-methyl]-phenyl}-ethenyl) mutilin, 12-epi-12-desvinyl-14-O-{{4-[(2-Amino-acetylamino)-methyl]-cyclohexylsulfanyl}-acetyl}-12-[2-{4-[(2-amino-ethylamino)-methyl]-phenyl}-ethyl) mutilin, 12-epi-12-desvinyl-14-O-[(Azepan-4-ylsulfanyl)-acetyl]-12-[2-(4-Aminomethyl-phenyl)-ethyl]-mutilin, 12-epi-12-desvinyl-14-O-[(Azepan-4-ylsulfanyl)-acetyl]-12-((E)-2-pyridin-3-yl-ethenyl) mutilin, 12-epi-12-desvinyl-14-O-[(Azepan-4-ylsulfanyl)-acetyl]-12-((E)-2-{4-[(2-Amino-ethylamino)-methyl]-phenyl}-ethenyl) mutilin, 12-epi-12-desvinyl-14-O-[(Azepan-4-ylsulfanyl)-acetyl]-12-[2-{4-[(2-amino-ethylamino)-methyl]-phenyl}-ethyl) mutilin, 12-epi-12-desvinyl-14-O-[(Azepan-4-ylsulfanyl)-acetyl]-12-((E)-2-{4-[(2-amino-ethylamino)-methyl]-3-fluoro-phenyl}-ethenyl) mutilin, 12-epi-14-O-{[1-(2-Amino-acetyl)-piperidin-4-yl-sulfanyl]-acetyl}-12-((E)-2-{4-[(2-amino-ethylamino)-methyl]-phenyl}-ethenyl) mutilin, 12-epi-14-O-{[1-(2-Amino-acetyl)-piperidin-4-yl-sulfanyl]-acetyl}-12-[2-{4-[(2-amino-ethylamino)-methyl]-phenyl}-ethyl) mutilin, 12-epi-12-desvinyl-14-O-[(5-Aminomethyl-pyridin-2-ylsulfanyl)-acetyl]-12-[2-(4-aminomethyl-benzoylamino)-ethyl] mutilin, 12-epi-12-desvinyl-14-O-[(Piperidin-4-ylsulfanyl]-acetyl]-12-[2-(3-methyl-pyrazin-2-yl)-ethenyl]-mutilin.

j) the compound is 12-epi-12-desvinyl-14-O-[(Piperidin-4-ylsulfanyl]-acetyl]-12-[2-(3-methyl-pyrazin-2-yl)-ethenyl]-mutilin.

Compounds as defined according to a) to i) are generally known from WO 2015/110481 A1, the disclosure of which is incorporated herein by reference. The particular compound as defined according to j), i.e. a compound according to formula (VIII)

(VIII)

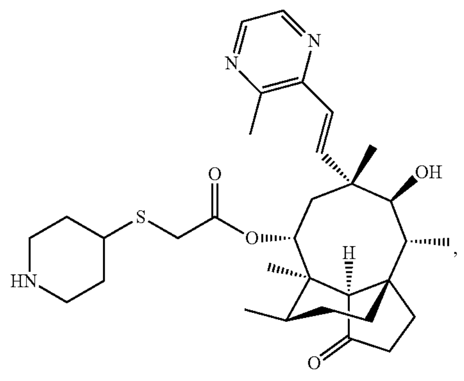

is disclosed in WO 2021/209596, the disclosure of which is incorporated herein by reference, too. In the following, the 12-epi-mutilin as defined according to j) or formula (VIII) is also referred to as “BC-9842”.

EXAMPLES

The trivial name mutilin refers to the IUPAC systematic name (1S,2R,3S,4S,6R,7R,8R,14R)-3,6-dihydroxy-2,4,7,14-tetramethyl-4-vinyl-tricyclo[5.4.3.$0^{1,8}$]tetradecan-9-one.

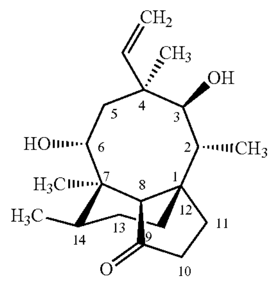

In the following examples, pleuromutilin derivatives are numbered in analogy to the mutilin numbering system described by H. Berner (Berner, H.; Schulz, G.; Schneider H. *Tetrahedron* 1980, 36, 1807-1811):

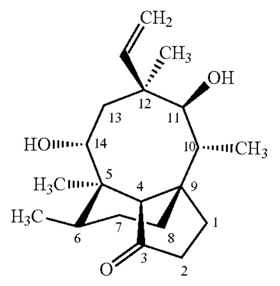

In the compounds of the present invention, e.g. in the compounds of examples 1 to 3, the stereochemistry of the methyl group at position 12 (and in turn also the stereochemistry of the second group attached in position 12 of the mutilin ring) is inverted (epi-mutilin derivatives) and in addition the vinyl group is altered and various substituents instead of vinyl have been introduced:

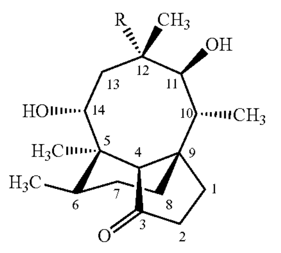

12-Epi-pleuromutilin and 14-O-chloroacetyl-12-epi-mutilin as mentioned below are compounds of the formulae:

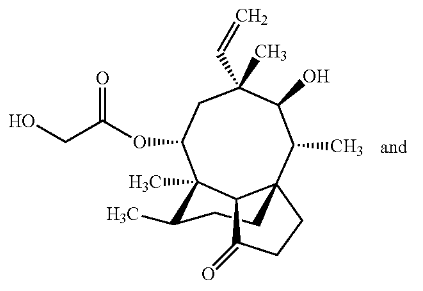

and

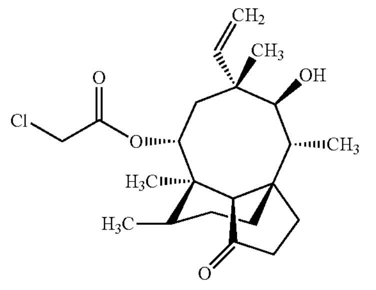

respectively.

Methods of preparing 12-epi-pleuromutilin derivatives are disclosed for example in WO 2015/110481 A1. Alternatively, a synthetic approach via 14-O-chloroacetyl-12-epi-mutilin is available as disclosed in Example 1. 14-O-chloroacetyl-12-epi-mutilin is prepared as described in WO 2021/219399 A1.

Herein, including the examples and the reaction scheme the following abbreviations are used:

$^1$H-NMR proton nuclear magnetic resonance spectroscopy

° C. degrees Celsius

BOC tert-butyloxycarbonyl

DMF dimethylformamide

EtOAc ethyl acetate

MIC minimal inhibitory concentration m/z mass/charge ratio

MS mass spectrometry nm nanometer

Example 1

12-epi-12-Desvinyl-14-O-{[(3S,3aR,6S,6aS)-3-amino-2,3,3a,5,6,6a-hexahydrofuro[3,2-b]furan-6-yl] sulfanylacetyl}-12-[(E)-2-(3-pyridyl)-ethenyl]-mutilin dihydrochloride Step 1: S-[(3S,3aR,6S,6aS)-3-(tert-butoxycarbonylamino)-2,3,3a,5,6,6a-hexahydrofuro[3.2-b]furan-6-yl] ethanethioate To tert-Butyl N-[(3S,3aR,6R,6aR)-6-hydroxy-2,3,3a,5,6,6a-hexahydrofuro[3,2-b]furan-3-yl] carbamate (WO2003082260 Example I-OC) (7.00 g) in dichloromethane (50 mL) was added methanesulfonic anhydride (7.46 g) and triethylamine (6 mL) and stirred overnight at room temperature. The resulting reaction mixture was diluted with ethyl acetate and washed with water. The organic phase was dried and evaporated to dryness under reduced pressure. The evaporation residue was dissolved in DMF (300 mL), potassium thioacetate (42.4 g) was added and heated to 110° C. oil bath temperature under stirring, until reaction completion. The resulting reaction mixture was diluted with ethyl acetate and washed with water. The organic phase was dried and evaporated to dryness under reduced pressure. The evaporation residue was subjected to chromatography over silica gel using cyclohexane/EtOAc 5:1 to obtain the title compound (10 g) in the form of a light brown solid.

1H-NMR (400 MHZ, CDCl3, δ, ppm): 4.57-4.52, 4.50-4.43 (2m, 2×1H), 4.20-4.10, 4.00-3.92, 3.78-3.70 (3m, 3×2H), 2.28 (s, 3H, COCH3), 1.37 (s, 9H, Boc).

MS m/z: 348 [M+HCOO$^-$].

Step 2: 12-epi-14-O-{[(3S,3aR,6S,6aS)-3-(tert-Butoxycarbonylamino)-2,3,3a,5,6,6a-hexahydrofuro[3,2-b]furan-6-yl]sulfanylacetyl}-mutilin To 14-O-chloroacetyl-12-epi-mutilin (2.62 g) was added methanol (15 mL), tetrahydrofuran (3 mL), S-[(3S,3aR,6S,6aS)-3-(tert-butoxycarbonylamino)-2,3,3a,5,6,6a-hexahydrofuro[3,2-b]furan-6-yl] ethanethioate (2.00 g) and potassium carbonate solution (5M in water, 2.64 mL) and stirred overnight at room temperature. The resulting reaction mixture was concentrated to dryness, taken up in ethyl acetate and washed twice with half-saturated NaCl solution. The combined aqueous phases were extracted with ethyl acetate, then the combined organic phases were dried over anhydrous $Na_2SO_4$ and evaporated to dryness under reduced pressure. The evaporation residue was subjected to chromatography over silica gel using cyclohexane/EtOAc 3:2 to obtain the title compound (3.68 g) in the form of a colorless solid.

$^1$H-NMR (400 MHZ, CDCl3, δ, ppm, characteristic signals, mutilin numbering system): 5.74 (dd, 1H, H-19, J=17.2, 10.8 Hz), 5.63 (d, 1H, H-14, J=8.0 Hz), 5.26-5.16 (m, 2H, H-20), 4.75-4.55, 4.54-4.45, 4.20-4.05, 3.97-3.86, 3.77-3.62, 3.46-3.35 and 3.32-3.18 (7m, 12H, NH, isomannide, H-11, H-22), 1.58-1.39 (m, 12H, BOC, $CH_3$-15), 1.22 (s, 3H, $CH_3$-18), 0.95 (d, 3H, $CH_3$-17, J=6.8 Hz), 0.72 (d, 3H, $CH_3$-16, J=6.8 Hz). MS m/z: 666 [M+HCOO$^-$].

Step 3: 2-epi-12-Desvinyl-14-O-{[(3S,3aR,6S,6aS)-3-(tert-butoxycarbonylamino)-2,3,3a,5,6,6a-hexahydrofuro[3,2-b]furan-6-yl]sulfanylacetyl}-12-[(E)-2-(3-pyridyl)-ethenyl]-mutilin 3-Bromo-pyridine (0.49 mL, 3 eq.) and bis-(benzonitrile)-palladium(II)-chloride (247 mg, 0.4 eq.) were suspended in ethylene glycol (40 mL). Then example 1 step 2 product (1 g, 1 eq.), N-methyl-morpholine (1.41 mL, 8 eq.) and ethylene glycol (40 mL) were added subsequently and the resulting mixture was stirred at 100° C. for 10 hours. The reaction mixture was diluted with ethyl acetate (500 mL), extracted with HCl/NaCl solution (500 mL, 0.1 M aqueous HCl+500 mL 5% aqueous NaCl solution, 1:1) and twice with 5% aqueous NaCl solution (500 mL). The combined aqueous phases were washed with ethyl acetate (250 mL). All organic phases were combined, washed with saturated aqueous NaCl solution (250 mL), dried over anhydrous $Na_2SO_4$ and concentrated under reduced pressure. The evaporation residue was subjected to chromatography over silica gel using EtOAc as eluent to obtain the title compound (719 mg) as a colorless solid.

$^1$H-NMR (400 MHZ, CDCl3, δ, ppm, characteristic signals, mutilin numbering system): 8.76, 8.46, 7.86 and 7.40 (4m, 4H, aromat.), 6.48 and 6.43 (2d, 2H, H-19, H-20, J=16.4 Hz), 5.66 (d, 1H, H-14, J=8.4 Hz), 4.80-4.64, 4.64-4.57, 4.53-4.47, 4.18-4.08, 3.94-3.86, 3.76-3.64, 3.44-3.38 and 3.32-3.20 (8m, 12H, NH, isomannide, H-22, H-11), 1.50-1.35 (m, 15H, BOC, $CH_3$-15, $CH_3$-18), 0.99 (d, 3H, $CH_3$-17, J=6.8 Hz), 0.74 (d, 3H, $CH_3$-16, J=6.8 Hz). MS m/z: 699 [M+H$^+$], 743 [M+HCOO$^-$].

Step 4: 12-epi-12-Desvinyl-14-O-{[(3S,3aR,6S,6aS)-3-amino-2,3,3a,5,6,6a-hexahydrofuro[3,2-b]furan-6-yl]sulfanylacetyl}-12-[(E)-2-(3-pyridyl)-ethenyl]-mutilin dihydrochloride Example 1 step 3 product (719 mg) was dissolved in dichloromethane (24 mL) and trifluoroacetic acid (7 mL) was added. The reaction mixture was stirred for 1 hour at room temperature and evaporated to dryness. The resulting residual was dissolved in little dichloromethane and hydrogen chloride (2M in diethylether, 7 mL) was added, stirred for 1 hour at room temperature and filtered. The precipitate was washed with diethylether, dissolved in water and lyophilized to obtain the title compound (651 mg) as colorless solid.

$^1$H-NMR (400 MHZ, DMSO-d6, δ, ppm, characteristic signals, mutilin numbering system): 8.95-8.85, 8.76-8.43, 8.00-7.88 (3m, 7H, aromat., NH), 6.84 and 6.51 (2d, 2H, H-19, H-20, J=16.4 Hz), 5.56 (d, 1H, H-14, J=8.4 Hz), 4.80-4.60, 4.12-4.02, 3.98-3.80, 3.74-3.60 and 3.54-3.36 (5m, 11H, isomannide, H-22, H-11), 1.40 (s, 3H, $CH_3$-15), 1.21 (s, 3H, $CH_3$-18), 0.86 (d, 3H, $CH_3$-17, J=6.8 Hz), 0.67 (d, 3H, $CH_3$-16, J=6.8 Hz).

MS m/z: 599 [M+H$^+$], 633 [M+Cl$^-$], 643 [M+HCOO$^-$].

Example 2

12-epi-12-Desvinyl-14-O-{[(3S,3aR,6S,6aS)-3-amino-2,3,3a,5,6,6a-hexahydrofuro[3,2-b]furan-6-yl]sulfanylacetyl}-12-[(E)-2-(pyrimidin-5-yl)-ethenyl]-mutilin dihydrochloride Step 1: 2-epi-12-Desvinyl-14-O-{[(3S,3aR,6S,6aS)-3-(tert-butoxycarbonylamino)-2,3,3a,5,6,6a-hexahydrofuro[3,2-b]furan-6-yl]sulfanylacetyl}-12-[(E)-2-(pyrimidin-5-yl)-ethenyl]-mutilin The reaction was carried out analogously to example 1 step 3 (same scale and reaction time), using 5-Bromo-pyrimidine (767 mg, 3 eq.) instead of 3-bromo-pyridine as a starting material to obtain title compound (813 mg) as a colorless solid.

$^1$H-NMR (400 MHZ, CDCl3, δ, ppm, characteristic signals, mutilin numbering system): 9.10, 8.89 (2s, 3H, aromat.), 6.54 and 6.42 (2d, 2H, H-19, H-20, J=16.4 Hz), 5.65 (d, 1H, H-14, J-8.0 Hz), 4.74-4.62, 4.62-4.57, 4.53-4.47, 4.18-4.08, 3.97-3.87, 3.75-3.65, 3.44-3.39 and 3.32-3.20 (8m, 12H, NH, isomannide, H-22, H-11), 1.50-1.35 (m, 15H, BOC, $CH_3$-15, $CH_3$-18), 0.98 (d, 3H, $CH_3$-17, J=7.2 Hz), 0.74 (d, 3H, $CH_3$-16, J=6.8 Hz).

MS m/z: 700 [M+H$^+$], 744 [M+HCOO$^-$].

Step 2: 12-epi-12-Desvinyl-14-O-{[(3S,3aR,6S,6aS)-3-amino-2,3,3a,5,6,6a-hexahydrofuro[3,2-b]furan-6-yl]sulfanylacetyl}- 12-[(E)-2-(pyrimidin-5-yl)-ethenyl]-mutilin dihydrochloride Example 2 step 1 product (813 mg) was dissolved in dichloromethane (27.5 mL) and trifluoroacetic acid (8 mL) was added. The reaction mixture was stirred for 1.5 hours at room temperature and evaporated to dryness. The resulting residual was dissolved in little dichloromethane and hydrogen chloride (2M in diethylether, 8 mL) was added, stirred for 1 hour at room temperature and filtered. The precipitate was washed with diethylether, dissolved in water and lyophilized to obtain the title compound (668 mg) as pale yellow to yellow solid.

$^1$H-NMR (400 MHZ, DMSO-d6, δ, ppm, characteristic signals, mutilin numbering system): 9.02, 8.87 (2s, 3H, aromat.), 8.62 (s, 3H, NH), 6.72 and 6.33 (2d, 2H, H-19, H-20, J=16.4 Hz), 5.56 (d, 1H, H-14, J=8.0 Hz), 4.74-4.57, 4.13-4.03, 3.98-3.90, 3.72-3.60 and 3.57-3.35 (5m, 11H, isomannide, H-22, H-11), 1.40 (s, 3H, $CH_3$-15), 1.19 (s, 3H, $CH_3$-18), 0.85 (d, 3H, $CH_3$-17, J=6.8 Hz), 0.67 (d, 3H, $CH_3$-16, J=6.4 Hz). MS m/z: 600 [M+H$^+$], 634 [M+Cl$^-$], 644 [M+HCOO$^-$].

Example 3

12-epi-12-Desvinyl-14-O-{[(3S,3aR,6S,6aS)-3-amino-2,3,3a,5,6,6a-hexahydrofuro[3,2-b]furan-6-yl]sulfanylacetyl}-12-[(E)-2-(3-methyl-pyrazin-2-yl)-ethenyl]-mutilin dihydrochloride Step 1: 2-epi-12-Desvinyl-14-O-{[(3S,3aR,6S,6aS)-3-(tert-butoxycarbonylamino)-2,3,3a,5,6,6a-hexahydrofuro[3.2-b]furan-6-yl]sulfanylacetyl}-12-[(E)-2-(3-methyl-pyrazin-2-yl)-ethenyl]-mutilin The reaction was carried out analogously to example 1 step 3 (same scale, reaction at 110° C. for 24 hours), using 2-Bromo-3-methyl-pyrazine (1.11 g, 4 eq.) instead of 3-bromo-pyridine as a starting material to obtain the title compound (154 mg) as a slightly yellow solid.

$^1$H-NMR (400 MHz, CDCl3, δ, ppm, characteristic signals, mutilin numbering system): 8.40-8.28 (m, 2H, aromat.), 6.93 and 6.69 (2d, 2H, H-19, H-20, J=15.6 Hz), 5.66 (d, 1H, H-14, J=8.4 Hz), 4.75-4.45, 4.17-4.03, 3.95-3.87, 3.76-3.62, 3.46-3.36 and 3.33-3.20 (6m, 12H, NH, isomannide, H-22, H-11), 2.62 (s, 3H, $CH_3$-aromat.), 1.48-1.33 (m, 15H, BOC, $CH_3$-15, $CH_3$-18), 0.97 (d, 3H, $CH_3$-17, J=7.2 Hz), 0.73 (d, 3H, $CH_3$-16, J=6.8 Hz).

MS m/z: 714 [M+H$^+$], 758 [M+HCOO$^-$].

Step 2: 12-epi-12-Desvinyl-14-O-{[(3S,3aR,6S,6aS)-3-amino-2,3,3a,5,6,6a-hexahydrofuro[3,2-b]furan-6-yl]sulfanylacetyl}- 12-[(E)-2-(3-methyl-pyrazin-2-yl)-ethenyl]-mutilin dihydrochloride Example 3 step 1 product (284 mg) was dissolved in dichloromethane (9 mL) and trifluoroacetic acid (3 mL) was added. The reaction mixture was stirred for 1 hour at room temperature and evaporated to dryness. The resulting residual was dissolved in little dichloromethane and diethylether and hydrogen chloride (2M in diethylether, 3 mL) was added, stirred for 30 minutes at room temperature and filtered. The precipitate was dissolved in water and lyophilized to obtain the title compound (204 mg) as pale yellow to yellow solid.

$^1$H-NMR (400 MHZ, DMSO-d6, δ, ppm, characteristic signals, mutilin numbering system): 8.48 (bs, 3H, NH), 8.34 and 8.27 (2s, 2H, aromat.), 7.08 and 6.46 (2d, 2H, H-19, H-20, J=15.6 Hz), 5.53 (d, 1H, H-14, J=7.6 Hz), 4.70-4.53, 4.09-3.97, 3.95-3.83, 3.73-3.52 and 3.52-3.30 (5m, 11H, isomannide, H-22, H-11), 2.50 (s, 3H, $CH_3$-aromat.), 1.35 (s, 3H, $CH_3$-15), 1.18 (s, 3H, $CH_3$-18), 0.80 (d, 3H, $CH_3$-17, J=6.4 Hz), 0.62 (d, 3H, $CH_3$-16, J=6.4 Hz).

MS m/z: 614 [$M+H^+$], 648 [$M+Cl^-$], 658 [$M+HCOO^-$].

Example 4

The in vitro activity against bacteria including isolates that are resistant to Lefamulin was determined by standard broth microdilution according to the Clinical and Laboratory Standards Institute CLSI document (Performance Standards for Antimicrobial Susceptibility Testing) M100Ed29E (2019) and (Methods for Dilution Antimicrobial Susceptibility Test for Bacteria That Grow Aerobically) M07Ed11 (2018) or other years' versions thereof. The data were obtained using cation-adjusted Mueller Hinton broth medium (CAMHB).

Results for Examples 1 to 3 in comparison to the comparative compound Example 154 of WO 2015/110481 A1 (12-epi-12-desvinyl-14-O-[(azepan-4-ylsulfanyl)-acetyl]-12-((E)-2-pyridin-3-yl-ethenyl) mutilin hydrochloride) and Lefamulin are summarized in Table 1.

TABLE 1

| MIC [μg/mL] | Example 1 | Example 2 | Example 3 | Example 154 of WO 2015/110481 | Lefamulin |
|---|---|---|---|---|---|
| *Staphylococcus aureus* ATCC49951 | ≤0.03 | ≤0.03 | ≤0.03 | ≤0.03 | ≤0.03 |
| *Staphylococcus aureus* cfr (+) (n = 2) | 0.12-0.5 | 0.12-1 | 1 | 0.5-4 | 16 |
| *Staphylococcus aureus* vga(A) (+) | 0.5 | 1 | 1 | 2-4 | 8 |
| *Streptococcus pneumoniae* ATCC49619 | ≤0.03 | ≤0.03 | ≤0.03 | ≤0.03 | ≤0.03 |
| *Streptococcus agalactiae* lsa(E) (n = 2) | 0.06-0.12 | ≤0.03-0.06 | 0.5-1 | 4-8 | 16 |

The compounds of examples 1 to 3 exhibit MICs≤0.1 μg/ml against *Staphylococcus aureus* ATCC49951, and *Streptococcus pneumoniae* ATCC49619. In addition, the compounds of Examples 1 to 3 exhibit MICs≤2 μg/ml against Lefamulin resistant *Staphylococcus aureus* strains mediated by e.g. cfr or vga(A) and Lefamulin resistant *Streptococcus agalactiae* strains mediated by e.g. lsa(E) resistance mechanisms.

Example 5

The metabolic stability for compounds of the present invention was determined by using cryopreserved primary mouse or human hepatocytes. 1.00 to 2.63×$10^5$ cells/mL in Krebs-Henseleit buffer (KHB) were incubated in the absence and the presence of 1 μg/mL of the test compounds at 37° C., 5% $CO_2$ for 4 hours (in triplicate). Test compounds were dissolved in dimethyl sulfoxide (DMSO) and further diluted with KHB, so that the DMSO concentration in the assay was ≤0.2%. To evaluate the non-enzymatic degradation under assay conditions, a sample of each test compound was incubated also in the absence of hepatocytes. Samples were taken immediately and after 4 hours of incubation. The incubation was stopped by adding the same volume of acetonitrile, vortexing and, freezing the reaction mixture. After thawing, vortexing, and centrifugation, the centrifugate was diluted with acidified (1% formic acid) water and analyzed for parent compound disappearance or metabolite appearance using LC/MS. The metabolic stability value corresponds to the remaining parent compound in % after 4 hours of incubation.

Results for Examples 1 to 3 in comparison to Example 154 from WO 2015/110481 A1 are summarized in Table 2.

TABLE 2

| | Metabolic stability against primary hepatocytes [% parent compound] | | | |
|---|---|---|---|---|
| | Example 1 | Example 2 | Example 3 | Example 154 from WO 2015/110481 |
| mouse | 57.1% | 63.8% | 58.9% | 0% |
| human | 25.3% | 54.9% | 62.4% | 0% |

Examples 1 to 3 display a metabolic stability of ≥50% after incubation with primary mouse and ≥20% after incubation with primary human hepatocytes. Especially in in comparison to the low metabolic stability of Example 154 from WO 2015/110481, this represents a valid improvement towards their usability as drug substance.

Example 6

The cytotoxicity for compounds of the present invention was determined using a human hepatocyte assay. Primary human hepatocytes were incubated with various test compound concentrations (in triplicate) for 2 hours. Viability of cells is then measured by the luminescence ATPlite detection assay system according to the manufacturer (Perkin Elmer). ATP is a marker for cell viability because it is present in all metabolically active cells and the concentration declines very rapidly when the cells undergo necrosis or apoptosis. The ATPlite assay system is based on the production of light caused by the reaction of ATP with added luciferase and D-luciferin, where the emitted light is proportional to the ATP concentration (within certain limits).

Results for Examples 1 to 3 in comparison to Example 154 from WO 2015/110481 A1 are summarized in Table 3.

TABLE 3

| | Example 1 | Example 2 | Example 3 | Example 154 from WO 2015/110481 |
|---|---|---|---|---|
| Cytotoxicity $IC_{50}$ [μM] | 215 | >609 | >433 | <225 |

The high $IC_{50}$ values for the cytotoxicity of the compounds according to the invention, especially for the compounds of Examples 2 and 3, confirm their excellent tolerability and promising safety profile as medicament.

Example 7

The in vitro activity against several bacteria of the genus *Cutibacterium* was investigated for several 12-epi-mutilines. The bacteria formerly known as *Propionibacterium* include *Cutibacterium acnes*, which is associated with or known to mediate acne. MIC values were determined by standard agardilution according to the Clinical and Laboratory Standards Institute CLSI document (Methods for Antimicrobial Susceptibility Testing of Anaerobic Bacteria, M11Ed09 (2018) or other years' versions thereof. The data were determined using an inoculum of grown on Brucella agar plates at 35° C. for 48 h, suspended in Thioglycolate medium at a density of McFarland of 1-1.5 and spotted on Wilkins-Chalgren-Agar (corresponding to $10^4$ colony forming units per spot) containing test compounds at various 2-fold dilutions. MICs were read after 48 h of incubation at 37° C. under anaerobic conditions.

Results for Examples 1 to 3, the further 12-epi-mutilin BC-9842 and Lefamulin are summarized in Table 4.

TABLE 4

| MIC [μg/mL] | Example 1 | Example 2 | Example 3 | BC-9842 | Lefamulin |
|---|---|---|---|---|---|
| *Cutibacterium acnes* (n = 5) | ≤0.015-0.12 | ≤0.015-0.12 | 0.03-0.5 | 0.03-0.05 | 0.03-0.5 |
| *Cutibacterium avidum* (n = 5) | ≤0.015-0.06 | ≤0.015-0.06 | 0.03-0.25 | ≤0.015-0.25 | 0.03-0.06 |
| *Cutibacterium granulosum* (n = 7) | ≤0.015-0.03 | ≤0.015-0.03 | ≤0.015-0.12 | ≤0.015-0.12 | ≤0.015-0.25 |

The compounds of Examples 1 to 3 as well as BC-9842 exhibit MICs values as good as Lefamulin or slightly better.

Example 8

Objective: To evaluate the antibacterial in vitro activity of 12-epi-mutilins, Lefamulin and antibiotic comparators of other classes against several *Borreliella* strains.

Methodology:

Minimal inhibitory concentrations (MIC) were determined against five (n=5) *Borreliella burgdorferi* isolates (ATCC 51990, 55131, 35211, 35210, 53899) and one (n=1) *Borreliella garinii* isolate (ATCC 51991) by broth microdilution technique (Dever, L. L., Jorgensen, J. H., Barbour, A. G. In vitro antimicrobial susceptibility testing of *Boreliella burgdorferi*: a microdilution MIC method and time-kill studies. *J Clin Microbiol.* 30(10), 2692-2697. (1992) doi: 10.1128/jcm.30.10.2692-2697.1992; Feng, J., Wang, T., Shi, W., et al. Identification of novel activity against *Boreliella burgdorferi* persisters using an FDA approved drug library. *Emerg Microb Infect* 3, e49 (2014) doi: 10.1038/emi.2014.53). The general procedures for broth microdilution were done according to the CLSI guidelines M7 and M100-S31 (CLSI. (2018) Methods for dilution antimicrobial susceptibility tests for bacteria that grow aerobically: Eleventh edition. M07; CLSI. (2021) Performance Standards for Antimicrobial Susceptibility Testing: Thirty-first Edition. M100-S31).

Briefly, *Borreliella* spp. were grown at 36° C. under microaerophilic conditions in BSK II medium until the logarithmic or stationary growth phase was reached. The growth phase was determined by semiquantitative measurement of active and dormant cells by fluorescence microscopy of cells stained with the fluorescent dyes SYBR Green I and propidium iodide. An inoculum of $10^5$-$10^6$ spirochetes/mL was used to inoculate broth microdilution plates containing serially 2-fold diluted test compounds. The inoculated microdilution plates were then covered with an adhesive film to ensure microaerophilic culture conditions and incubated at 36° C. for 5 days or until bacterial growth was observed in the positive control wells. MICs for the logarithmic growth phase cultures were read after 5 or 6 days of incubation (when the growth control showed good growth) and MICs for the stationary growth phase cultures were read after 8 days of incubation.

Results:

The resulting MIC values for the logarithmic and stationary growth phase cultures are summarized in Table 1 below. MIC results for single isolates varied slightly in various experiments but were within one 2-fold dilution factor (or at most two). Accordingly, the MIC values are indicated with ranges covering different experiments against *Borreliella* spp. (n=6) including *B. burgdorferi* (n=5) and *B. garinii* (n=1) in either logarithmic or stationary growth phase (Table 1).

TABLE 5

In vitro antibacterial activity of Lefamulin and comparator antibiotics against *Borreliella* spp.

| Compound | MIC (μg/mL) for Logarithmic Growth Phase Culture (n = 6) | MIC (μg/mL) for Stationary Growth Phase Culture (n = 6) |
|---|---|---|
| Lefamulin | ≤0.001-0.008 | ≤0.001-0.008 |
| Example 1 | ≤0.001-0.002 | ≤0.001-0.004 |
| Example 2 | ≤0.001-0.002 | ≤0.001-0.004 |
| Example 3 | ≤0.001-0.004 | ≤0.001-0.008 |
| BC-9842 | ≤0.001-0.004 | ≤0.001-0.004 |
| Doxycycline | ≤0.03-0.5 | ≤0.03-0.5 |
| Erythromycin | 0.002-0.016 | ≤0.001-0.004 |
| Azithromycin | ≤0.001-0.004 | ≤0.001-0.004 |

TABLE 5-continued

In vitro antibacterial activity of Lefamulin and comparator antibiotics against *Borreliella* spp.

| Compound | MIC (μg/mL) for Logarithmic Growth Phase Culture (n = 6) | MIC (μg/mL) for Stationary Growth Phase Culture (n = 6) |
|---|---|---|
| Amoxicillin | ≤0.03-0.12 | ≤0.03-0.12 |
| Cefuroxime | 0.016-0.25 | 0.016-0.25 |
| Ceftriaxone | ≤0.004-0.016 | ≤0.004-0.03 |
| Ciprofloxacin | 0.25-2 | 0.25-2 |
| Levofloxacin | 2-4 | 2-8 |
| Pleuromutilin | 0.12-1 | 0.12-2 |

The compounds of Examples 1 to 3 as well as BC-9842 showed activities comparable to Lefamulin or even better. The MICs for all Examples 1 to 3 ranged between ≤0.001 to 0.004 μg/mL for the logarithmic growth phase; and were similar for cultures in stationary growth phase (≤0.001-0.008 μg/mL). Lefamulin and the 12-epi-mutilinis were within the most active compounds when compared to other antibiotic classes that are used to treat Lyme disease including doxycycline, ceftriaxone, cefuroxime or azithromycin. The MIC values of Pleuromutilin were higher in about two orders of magnitude.

What is claimed is:

1. A compound of formula (I)

(I)

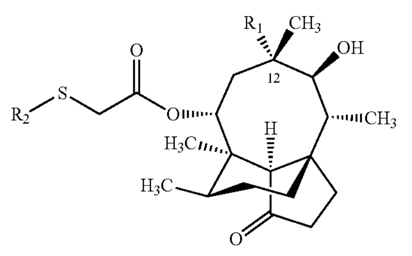

wherein $R_1$ is

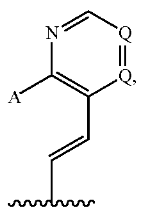

wherein A is a hydrogen atom or a $(C_{1-6})$ alkyl, and wherein any Q is independently from each other a nitrogen atom or CH, wherein $R_2$ is

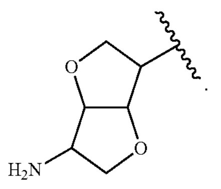

2. The compound according to claim 1, wherein A is a $(C_{1-3})$ alkyl selected from the group consisting of methyl, ethyl, 1-propyl, 2-propyl, and cyclopropyl.

3. The compound according to claim 1-er 2, wherein the compound is a compound of formula (II)

(II)

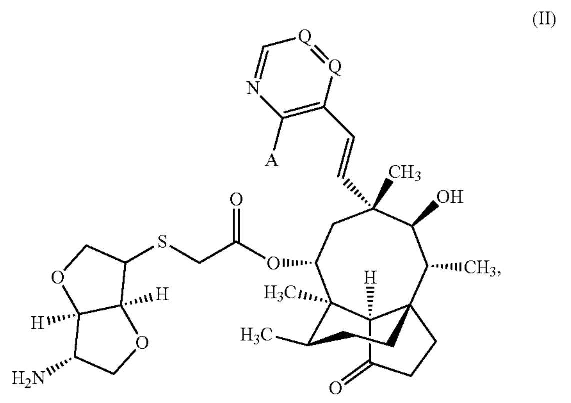

wherein A and Q are defined as in claim 1.

4. The compound according to claim 1, wherein the compound is selected from the group consisting of compounds of formula (III), (IV) and (V)

(III)

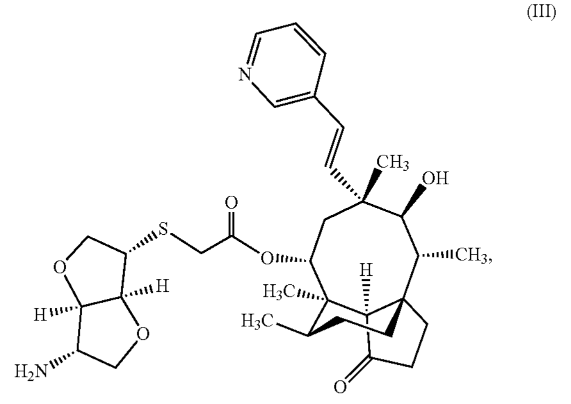

(IV)

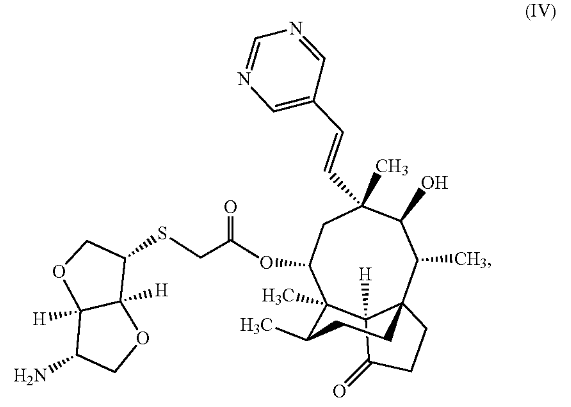

-continued (V)

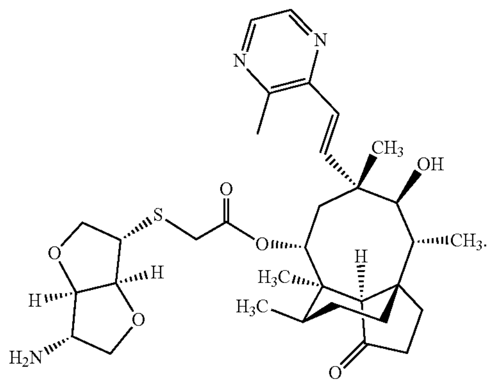

5. The compound according to claim 1, wherein the compound is in the form of a salt and/or solvate.

6. The compound according to claim 1, wherein A is methyl.

7. The compound according to claim 1, wherein the compound is in the form of a dihydrochloride salt.

8. A pharmaceutical drug composition comprising a compound of claim 1 and at least one pharmaceutical excipient.

9. The pharmaceutical drug composition according to claim 8, further comprising an additional pharmaceutically active agent.

10. A method of treatment or prevention of a disease mediated by bacteria selected from the group consisting of: staphylococci, streptococci, enterococci, Clostridia, Peptostreptococci, cutibacteria, *Listeria monocytogenes, Eubacterium lentum, Finegoldia magna, Anaerococcus prevotii, Peptoniphilus assaccharolyticus, Moraxella, Haemophilus*, Chlamydiae, Neisseriaceae, *Mycoplasma* spp., Fusobacteria, *Prevotella* spp., *Porphyromonas* spp., *Legionella*, spirochaetes, *Bacteroides fragilis, Acinetobacter lwoffii*, and combinations thereof, the method comprising a step of administering to a subject in need thereof a therapeutically effective amount of a compound of claim 1.

11. The method according to claim 10, wherein the disease is mediated by bacteria selected from the group consisting of staphylococci, streptococci, cutibacteria, spirochaetes, and combinations thereof.

12. The method according to claim 10, wherein the disease is mediated by bacteria resistant to Lefamulin.

13. The method according to claim 12, wherein the bacteria has a Lefamulin resistance mediated by vga(A), Isa(E) or cfr.

* * * * *